US007432263B2

(12) United States Patent
Pulici

(10) Patent No.: US 7,432,263 B2
(45) Date of Patent: Oct. 7, 2008

(54) AMINO-PHTHALAZINONE DERIVATIVES ACTIVE AS KINASE INHIBITORS, PROCESS FOR THEIR PREPARATION AND PHARMACEUTICAL COMPOSITIONS CONTAINING THEM

(75) Inventor: Maurizio Pulici, Caponago (IT)

(73) Assignee: Pfizer Italia, S.r.l., Rome (IT)

( * ) Notice: Subject to any disclaimer, the term of this patent is extended or adjusted under 35 U.S.C. 154(b) by 279 days.

(21) Appl. No.: 10/486,463

(22) PCT Filed: Jul. 30, 2002

(86) PCT No.: PCT/EP02/08544

§ 371 (c)(1),
(2), (4) Date: Sep. 9, 2004

(87) PCT Pub. No.: WO03/014090

PCT Pub. Date: Feb. 20, 2003

(65) Prior Publication Data
US 2005/0020583 A1 Jan. 27, 2005

(51) Int. Cl.
A61K 31/498 (2006.01)
A61K 31/502 (2006.01)
C07D 237/32 (2006.01)
C40B 40/04 (2006.01)
C07D 307/83 (2006.01)
C07D 407/06 (2006.01)
C07D 405/06 (2006.01)
C07F 9/09 (2006.01)

(52) U.S. Cl. .................. 514/249; 514/251; 544/237; 506/15; 549/216; 549/304; 546/283.1

(58) Field of Classification Search ............. 544/237, 544/279, 260; 514/251, 249, 264.11; 977/794; 506/15
See application file for complete search history.

(56) References Cited

FOREIGN PATENT DOCUMENTS

| EP | 0600831 A1 | 6/1994 |
| EP | 0634404 A1 * | 1/1995 |
| GB | 871753 A | 6/1961 |
| JP | 09061961 A | 3/1997 |
| JP | 10287658 A | 10/1998 |
| WO | WO 98/35958 A1 | 8/1998 |
| WO | WO 0061556 * | 10/2000 |

OTHER PUBLICATIONS

Clare, et al., J. Biol. Chem., vol. 276, No. 51, Dec. 21, 2001, pp. 48292-48299.*
Georgieva, et al., J. Clin. Pathol. 2001; 54:229-235.*
Takahashi, et al., Mol. Cancer Ther., 2005,; 4(7), Jul. 2005.*
Attached printout from the Leukemia & Lymphoma Society website, <http://www.leukemia-lymphoma.org/all_page?item_id=7026>, downloaded Jul. 12, 2007.*
Printout from the Leukemia & Lymphoma Society website, <http://www.leukemia-lymphoma.org/all_page?item_id=7030 &viewmode=print>, downloaded Jul. 13, 2007.*
Printout on viral infections from the Medline Plus website, <http://www.nlm.nih.gov/medlineplus/viralinfections.html>, downloaded Jul. 12, 2007.*
Attached printout from the Johns Hopkins Medical Institutions website, <http://autoimmune.pathology.jhmi.edu/diseases.cfm.> downloaded Jul. 16, 2007.*
Disorders Index of the National Institute of Neurological Disorders and Stroke, http://www.ninds.nih.gov/disorders/disorder_index.htm?css=print, (NINDS Index).*
Patton, et al., J. Pharmacol & Exp. Therap., vol. 239, No. 2, pp. 597-605.*
Blain, et al., J. of Biol. Chem., vol. 272,, No. 41, Oct. 10, 1997, 25863-25872.*
BBC News/Health, Killer Breast Cancer Therapy Hope, <http://newsvote.bbc.co.uk/mpapps/pagetooles/print/news.bbc.co.uk/1/hi/health/4619900.stm>, downloaded Jan. 31, 2007.*
Masuda, et al., Oncogene (Feb. 20, 2003) 22, 1012-1023.*
Ito, et al., Anticancer Research, 2004, Vo. 24, No. 1, pp. 259+ (Abstract).*
Mito, et al., Leuk. Lymphoma, Feb. 2005, 46(2): 225+ (PubMed abstract).*
Verschuren, et al., J. Gen. Virology (2004), 85, 1347-1361.*
(<<http://www.uspto.gov/web/offices/pac/dapp/1pecba.htm#7>> Enablement Decision Tree, Example F, situation 1.*
Viral Defense Found., <http://www.viraldefense.org/mission.htm>, downloaded May 23, 2007.*
Visiting Nurse Assns. of America, <http://www.vnaa.org/vnaa/gen/Germ_Protection_Center_Cold_and_Flu_Resources,html...>, downloaded May 23, 2007.*

(Continued)

Primary Examiner—James Wilson
Assistant Examiner—Cecilia M Jaisle
(74) Attorney, Agent, or Firm—Scully, Scott, Murphy & Presser, P.C.

(57) ABSTRACT

Compounds which are amino-phthalazinone derivatives according to formula 1 and pharmaceutically acceptable salts thereof, together with pharmaceutical compositions comprising them are disclosed; these compounds or compostions are useful in the treatment of diseases caused by and/or associated with an altered protein kinase activity such as cancer, cell proliferative disorders, Alzheimer's disease, viral infections, autoimmune diseases and neurodegenerative disorders.

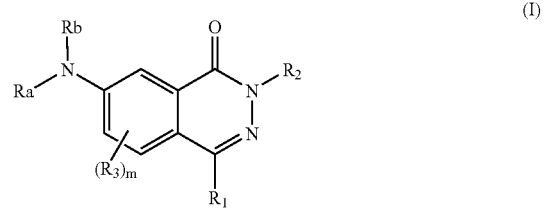

(I)

23 Claims, No Drawings

OTHER PUBLICATIONS

Printout from the Wikipedia website < http://en.wikipedia.org/wiki/Derivative_%28chemistry%29> providing a chemical definition of "derivative," downloaded Jul. 21, 2007.*

Philip Cohen, *The Development and Therapeutic Potential of Protein Kinase Inhibitors*, Current Opinion in Chemical Biology, vol. 3, pp. 459-465, (1999).

S. S. Berg, *Bisquaternary Salts Related to Quinapyramine (Antrycide) Replacement of the Quinoline Nucleus by Other Heterocycles*, Journal of Chem Soc. pp. 5275-5284, (1961).

Brian D. Palmer, *Structure-Activity Relationships for 5-Substituted 1-Phenylbenzimidazoles as Selective Inhibitors of the Platelet-Derived Growth Factor Receptor*, Journal of Medical Chemistry, vol. 42, pp. 2373-2382, (1999).

* cited by examiner

AMINO-PHTHALAZINONE DERIVATIVES ACTIVE AS KINASE INHIBITORS, PROCESS FOR THEIR PREPARATION AND PHARMACEUTICAL COMPOSITIONS CONTAINING THEM

The present invention relates to amino-phthalazinone derivatives active as kinase inhibitors and, more in particular, it relates to 7-amino-phthalazin-1-one derivatives, to a process for their preparation, to pharmaceutical compositions comprising them and to their use as therapeutic agents, particularly in the treatment of diseases linked to disregulated protein kinases.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

It is an object of the invention to provide compounds which are useful in therapy as agents against a host of diseases caused by and/or associated to a disregulated protein kinase activity.

It is another object to provide compounds which are endowed with multiple protein kinase inhibiting activity.

The present inventors have now discovered that some 7-amino-phthalazin-1-one derivatives, hereinafter shortly referred to as amino-phthalazinone derivatives or amino-phthalazinones, are endowed with multiple protein kinase inhibiting activity and are thus useful in therapy in the treatment of diseases associated with disregulated protein kinases.

More specifically, the amino-phthalazinones of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these amino-phthalazinones are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 117, 741-749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention are useful as cyclin dependent kinase (cdk) inhibitors and also as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases.

Some amino-phthalazinone and amino-phthalazinedione derivatives are known in the art, as chemical intermediates, as therapeutic agents and even as protein kinase inhibitors.

As an example, the compounds N-[3-[2,4-bis(1,1-dimethylpropyl)phenoxy]propyl]-N'-(3,4-dihydro-4-oxo-6-phthalazinyl)-urea and 2-[2,4-bis(1,1-dimethylpropyl)phenoxy]-N-(3,4-dihydro-4-oxo-6-phthalazinyl)-butanamide are disclosed as heat development image forming agents, in JP-A-09061961 by Heisei.

The compound N-[3,4-dihydro-3-[4-[4-(1-naphthalenyl)-1-piperazinyl]butyl]-4-oxo-6-phthalazinyl]-acetamide is disclosed in JP-A-10287658 by Heisei, as a serotoninergic/dopaminergic agent.

The compounds N-[3,4-dihydro-4-oxo-1-(4-pyridinylmethyl)-6-phthalazinyl]-acetamide and N-[3,4-dihydro-4-oxo-1-(4-pyridinylmethyl)-6-phthalazinyl]-2,2,2-trifluoro-acetamide are disclosed in WO 98/35958 by Novartis, as synthetic intermediates for the preparation of anilino-phthalazines, as VEGF receptor tyrosine kinase inhibitors. In addition to the above, phthalazinedione or phthalazinone derivatives bearing substituted amino groups in both positions 6 and 7 of the ring such as, for instance, 7-(cyclohexylamino)-6-phenylamino-1 (2H)-phthalazinone and 6,7-bis(phenylamino)-1(2H)-phthalazinone, are disclosed in EP-A-600831 by Ciba-Geigy as protein kinase inhibitors.

Accordingly, the present invention provides a method for treating diseases caused by and/or associated with an altered protein kinase activity, by administering to a mammal in need thereof an effective amount of an amino-phthalazinone derivative represented by formula (I):

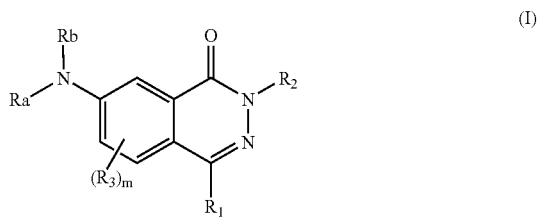

wherein
Ra and Rb are, each independently, a hydrogen atom or a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or one of Ra or Rb is hydrogen or an optionally substituted straight or branched $C_1$-$C_6$ alkyl group, and the other is a group selected from —COR', —CONHR', —COOR' or —SO$_2$R', wherein R' is hydrogen or an optionally substituted group selected from alkyl, cycloalkyl, cycloalkylalkyl, aryl, arylalkyl, heterocyclyl or heterocyclylalkyl, as set forth above;

$R_1$ is a group of formula —CHR$_4$R$_5$ wherein $R_4$ and $R_5$ are, each independently, hydrogen or an optionally substituted group selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_1$ is a group of formula —NHR', —NR'COR", —NR'CONHR" or —NR'SO$_2$R", wherein R" has the above reported meanings other than hydrogen, and R" is hydrogen or has the meanings set forth above for R';

$R_2$ is a hydrogen atom or it is a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur;

any $R_3$, being placed in one or more of the free positions 5, 6 and 8 of the phthalazinone ring are, independently from each other, halogen, nitro, carboxy, cyano or a group optionally further substituted selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_3$ is a group selected from —COR', —CONHR', —SO$_2$R', —NR'R", —NR'COR", —NR'CONHR' or —NR'SO$_2$R", wherein R' and R" are, the same or different, hydrogen or a group as set forth above;

m is 0 or an integer from 1 to 3;

or a pharmaceutically acceptable salt thereof.

In a preferred embodiment of the method described above, the disease caused by and/or associated with an altered protein kinase activity is selected from the group consisting of cancer, cell proliferative disorders, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth muscle cell proliferation associated with atherosclerosis, pulmonary fibrosis, arthritis glomerulonephritis and post-surgical stenosis and restenosis.

In addition, the method object of the present invention, also provides tumor angiogenesis and metastasis inhibition. The present invention further provides an amino-phthalazinone derivative represented by formula (I)

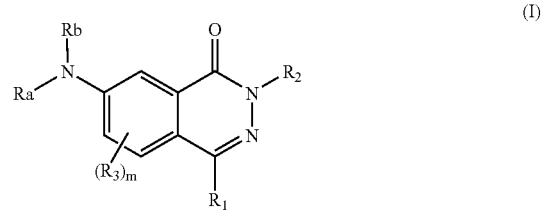

wherein

Ra and Rb are, each independently, a hydrogen atom or a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or one of Ra or Rb is hydrogen or an optionally substituted straight or branched $C_1$-$C_6$ alkyl group, and the other is a group selected from —COR', —CONHR', —COOR' or —SO$_2$R', wherein R' is hydrogen or an optionally substituted group selected from alkyl, cycloalkyl, cycloalkylalkyl, aryl, arylalkyl, heterocyclyl or heterocyclylalkyl, as set forth above;

$R_1$ is a group of formula —CHR$_4$R$_5$ wherein $R_4$ and $R_5$ are, each independently, hydrogen or an optionally substituted group selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_1$ is a group of formula —NHR', —NR'COR", —NR'CONHR" or —NR'SO$_2$R", wherein R' has the above reported meanings other than hydrogen, and R" is hydrogen or has the meanings set forth above for R';

$R_2$ is a hydrogen atom or it is a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur;

any $R_3$, being placed in one or more of the free positions 5, 6 and 8 of the phthalazinone ring are, independently from each other, halogen, nitro, carboxy, cyano or a group optionally further substituted selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_3$ is a group selected from —COR', —CONHR', —SO$_2$R', —NR'R", —NR'COR", —NR'CONHR' or —NR'SO$_2$R", wherein R' and R" are, the same or different, hydrogen or a group as set forth above;

m is 0 or an integer from 1 to 3;

or a pharmaceutically acceptable salt thereof;

the compounds N-[3,4-dihydro-4-oxo-1-(4-pyridinylmethyl)-6-phthalazinyl]-acetamide and N-[3,4-dihydro-4-oxo-1-(4-pyridinylmethyl)-6-phthalazinyl]-2,2,2-trifluoro-acetamide, being excluded.

The compounds of formula (I), object of the present invention, may have asymmetric carbon atoms and may therefore exist either as racemic admixtures or as individual optical isomers.

Accordingly, all the possible isomers and their admixtures and of both the metabolites and the pharmaceutically acceptable bio-precursors (otherwise referred to as pro-drugs) of the compounds of formula (I), as well as any therapeutic method of treatment comprising them, are also within the scope of the present invention.

As used herein, unless otherwise specified, with the term halogen atom we intend a chlorine, bromine, fluorine or iodine atom.

With the term straight or branched $C_1$-$C_6$ alkyl we intend a group such as, for instance, methyl, ethyl, n-propyl, isopropyl, n-butyl, isobutyl, sec-butyl, tert-butyl, n-pentyl, n-hexyl and the like.

With the term $C_3$-$C_6$ cycloalkyl we intend a group such as, for instance, cyclopropyl, cyclobutyl, cyclopentyl or cyclohexyl.

With the term aryl we intend a mono-, bi- or poly- either carbocyclic as well as heterocyclic hydrocarbon with from 1 to 4 ring moieties, either fused to each other or linked by single bonds, wherein at least one of the carbocyclic or heterocyclic rings is aromatic.

Non limiting examples of aryl groups are, for instance, phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolylphenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

With the term 5 to 7 membered heterocyclyl, hence encompassing aromatic heterocyclic groups also referred to as aryl groups, we further intend a saturated or partially unsaturated 5 to 7 membered carbocycle wherein one or more carbon atoms are replaced by 1 to 3 heteroatoms such as nitrogen, oxygen and sulfur.

Besides the above heteroaryl groups, additional examples of 5 to 7 membered heterocyclyl groups, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azepine, diazepine and the like.

According to the present formula (I), it is clear to the skilled man that when m is 0 there are no $R_3$ groups or, in other words, the positions 5, 6 and 8 of the phthalazinone ring, as per the numbering system below, are unsubstituted or hydrogen substituted

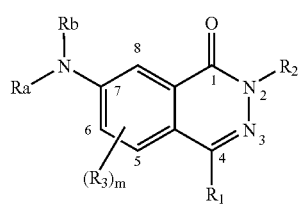

(I)

Likewise, when m is 1 or 2, one or two $R_3$ substituents, the same or different from each other, are present in one or two of the positions 5, 6 or 8; finally, when m is 3, all of the available 5, 6 and 8 positions are occupied by $R_3$ groups, the same or different, as above indicated.

According to the above meanings provided to Ra, Rb, R', R", $R_2$, $R_3$, $R_4$ and $R_5$ substituents, any of the above groups may be further optionally substituted in any of the free positions by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

Among these latter groups and unless otherwise specified in the present description, with the term perfluorinated alkyl we intend a straight or branched $C_1$-$C_6$ alkyl group as above defined, wherein more than one hydrogen atom are replaced by fluorine atoms. Example of perfluorinated alkyl groups are, for instance, trifluoromethyl, 2,2,2-trifluoroethyl, 1,2-difluoroethyl, 1,1,1,3,3,3-hexafluoropropyl-2-yl and the like.

With the term alkenyl or alkynyl we intend a straight or branched $C_2$-$C_6$ alkenyl or alkynyl group such as, for instance, vinyl, allyl, isopropenyl, 1-, 2- or 3-butenyl, isobutylenyl, hexenyl, ethynyl, 1- or 2-propynyl, butynyl and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkoxy, heterocyclyloxy, heterocyclylalkoxy, alkylcarbonyloxy and the like, has to be intended as conventionally construed from the parts to which it derives.

As an example, the term heterocyclyl-alkoxy stands for an alkoxy (e.g. alkyl-oxy) group further substituted by a heterocyclyl group.

Pharmaceutically acceptable salts of the compounds of formula (I) are the acid addition salts with inorganic or organic, e.g. nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulfonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

A first class of preferred compounds of the invention is represented by the compounds of formula (I) wherein one of Ra or Rb is a hydrogen atom or an optionally substituted straight or branched $C_1$-$C_6$ alkyl group and the other is a group —COR' wherein R' is an optionally substituted group selected from alkyl, cycloalkyl, cycloalkylalkyl, aryl, arylalkyl, heterocyclyl or heterocyclylalkyl, as set forth above, and $R_1$, $R_2$, $R_3$ and m are as above defined.

More preferred, within this class, are the compounds of formula (I) wherein $R_1$ is a group —$CHR_4R_5$ wherein $R_4$ and $R_5$ are as above defined, $R_2$ is hydrogen and m is 0.

Another class of preferred compounds of the invention is represented by the compounds of formula (I) wherein one of Ra or Rb is a hydrogen atom or an optionally substituted straight or branched $C_1$-$C_6$ alkyl group and the other is a group —CONHR' wherein R' is a hydrogen atom or an optionally substituted group selected from alkyl, cycloalkyl, cycloalkylalkyl, aryl, arylalkyl, heterocyclyl or heterocyclylalkyl, as set forth above, and $R_1$, $R_2$, $R_3$ and m are as above defined.

More preferred, within this class, are the compounds of formula (I) wherein $R_1$ is a group —$CHR_4R_5$ wherein $R_4$ and $R_5$ are as above defined, $R_2$ is hydrogen and m is 0.

Another class of preferred compounds of the invention is represented by the compounds of formula (I) wherein one of Ra or Rb is a hydrogen atom or an optionally substituted straight or branched $C_1$-$C_6$ alkyl group and the other is a group —COOR' wherein R' is a hydrogen atom or an optionally substituted group selected from alkyl, cycloalkyl, cycloalkylalkyl, aryl, arylalkyl, heterocyclyl or heterocyclylalkyl, as set forth above, and $R_1$, $R_2$, $R_3$ and m are as above defined.

More preferred, within this class, are the compounds of formula (I) wherein $R_1$ is a group —$CHR_4R_5$ wherein $R_4$ and $R_5$ are as above defined, $R_2$ is hydrogen and m is 0.

Another class of preferred compounds of the invention is represented by the compounds of formula (I) wherein one of Ra or Rb is a hydrogen atom or an optionally substituted straight or branched $C_1$-$C_6$ alkyl group and the other is a group —$SO_2R'$ wherein R' is an optionally substituted group selected from alkyl, cycloalkyl, cycloalkylalkyl, aryl, arylalkyl, heterocyclyl or heterocyclylalkyl, as set forth above, and $R_1$, $R_2$, $R_3$ and m are as above defined.

More preferred, within this class, are the compounds of formula (I) wherein $R_1$ is a group —$CHR_4R_5$ wherein $R_4$ and $R_5$ are as above defined, $R_2$ is hydrogen and m is 0.

Another class of preferred compounds of the invention is represented by the compounds of formula (I) wherein Ra and Rb are both hydrogen atoms and $R_1$, $R_2$, $R_3$ and m are as above defined.

More preferred, within this class, are the compounds of formula (I) wherein $R_1$ is a group —$CHR_4R_5$ wherein $R_4$ and $R_5$. are as above defined, $R_2$ is hydrogen and m is 0.

Another class of preferred compounds of the invention is represented by the compounds of formula (I) wherein one of Ra or Rb is a hydrogen atom or an optionally substituted straight or branched $C_1$-$C_6$ alkyl and the other is a group, optionally further substituted, selected from alkyl, cycloalkylalkyl, arylalkyl or heterocyclylalkyl as set forth above, and $R_1$, $R_2$, $R_3$ and m are as above defined.

More preferred, within this class, are the compounds of formula (I) wherein $R_1$ is a group —$CHR_4R_5$ wherein $R_4$ and $R_5$ are as above defined, $R_2$ is hydrogen and m is 0.

Specific examples of preferred compounds of formula (I) of the invention, optionally in the form of pharmaceutically acceptable salts, are:

1. 4-(4-Oxo-6-propionylamino-3,4-dihydro-phthalazin-1-yl-methyl)-benzoic acid methyl ester;
2. 4-[4-Oxo-6-(4-trifluoromethyl-benzoylamino)-3,4-dihydro-phthalazin-1-ylmethyl]-benzoic acid methyl ester;
3. 4-{6-[(Furan-2-carbonyl)-amino]-4-oxo-3,4-dihydro-phthalazin-1-ylmethyl}-benzoic acid methyl ester;
4. 4-[6-(3,4-Dimethoxy-benzoylamino)-4-oxo-3,4-dihydro-phthalazin-1-ylmethyl]-benzoic acid methyl ester;
5. 4-[6-(3-Cyclopentyl-propionylamino)-4-oxo-3,4-dihydro-phthalazin-1-ylmethyl]-benzoic acid methyl ester;
6. 4-[4-Oxo-6-(2-propyl-pentanoylamino)-3,4-dihydro-phthalazin-1-ylmethyl]-benzoic acid methyl ester;
7. 4-{4-Oxo-6-[3-(3-trifluoromethyl-phenyl)-ureido]-3,4-dihydro-phthalazin-1-ylmethyl}-benzoic acid methyl ester;
8. 4-{6-[3-(3-Methoxy-phenyl)-ureido]-4-oxo-3,4-dihydro-phthalazin-1-ylmethyl}-benzoic acid methyl ester;
9. 4-[4-Oxo-6-(3-p-tolyl-ureido)-3,4-dihydro-phthalazin-1-ylmethyl]-benzoic acid methyl ester;
10. 4-{6-[3-(2,4-Difluoro-phenyl)-ureido]-4-oxo-3,4-dihydro-phthalazin-1-ylmethyl}-benzoic acid methyl ester;
11. 4-{6-[3-(3,4-Dichloro-phenyl)-ureido]-4-oxo-3,4-dihydro-phthalazin-1-ylmethyl}-benzoic acid methyl ester;
12. 4-[4-Oxo-6-(3-pyridin-3-yl-ureido)-3,4-dihydro-phthalazin-1-ylmethyl]-benzoic acid methyl ester;
13. 4-(6-Amino-4-oxo-3,4-dihydro-phthalazin-1-ylmethyl)-benzoic acid methyl ester;
14. N-[1-(4-Chloro-3-fluoro-benzyl)-4-oxo-3,4-dihydro-phthalazin-6-yl]-propionamide;
15. N-[1-(4-Chloro-3-fluoro-benzyl)-4-oxo-3,4-dihydro-phthalazin-6-yl]-4-trifluoromethyl-benzamide;
16. Furan-2-carboxylic acid [1-(4-chloro-3-fluoro-benzyl)-4-oxo-3,4-dihydro-phthalazin-6-yl]-amide;
17. N-[1-(4-Chloro-3-fluoro-benzyl)-4-oxo-3,4-dihydro-phthalazin-6-yl]-3,4-dimethoxy-benzamide;
18. N-[1-(4-Chloro-3-fluoro-benzyl)-4-oxo-3,4-dihydro-phthalazin-6-yl]-3-cyclopentyl-propionamide;
19. 2-Propyl-pentanoic acid [1-(4-chloro-3-fluoro-benzyl)-4-oxo-3,4-dihydro-phthalazin-6-yl]-amide;
20. 1-[1-(4-Chloro-3-fluoro-benzyl)-4-oxo-3,4-dihydro-phthalazin-6-yl]-3-(3-trifluoromethyl-phenyl)-urea;
21. 1-[1-(4-Chloro-3-fluoro-benzyl)-4-oxo-3,4-dihydro-phthalazin-6-yl]-3-(3-methoxy-phenyl)-urea;
22. 1-[1-(4-Chloro-3-fluoro-benzyl)-4-oxo-3,4-dihydro-phthalazin-6-yl]-3-p-tolyl-urea;
23. 1-[1-(4-Chloro-3-fluoro-benzyl)-4-oxo-3,4-dihydro-phthalazin-6-yl]-3-(2,4-difluoro-phenyl)-urea;
24. 1-[1-(4-Chloro-3-fluoro-benzyl)-4-oxo-3,4-dihydro-phthalazin-6-yl]-3-(3,4-dichloro-phenyl)-urea;
25. 1-[1-(4-Chloro-3-fluoro-benzyl)-4-oxo-3,4-dihydro-phthalazin-6-yl]-3-pyridin-3-yl-urea;
26. 7-Amino-4-(4-chloro-3-fluoro-benzyl)-2H-phthalazin-1-one;
27. N-{1-[(E)-3-(4-Nitro-phenyl)-allyl]-4-oxo-3,4-dihydro-phthalazin-6-yl}-propionamide;
28. N-{1-[(E)-3-(4-Nitro-phenyl)-allyl]-4-oxo-3,4-dihydro-phthalazin-6-yl}-4-trifluoromethyl-benzamide;
29. Furan-2-carboxylic acid {1-[(E)-3-(4-nitro-phenyl)-allyl]-4-oxo-3,4-dihydro-phthalazin-6-yl}-amide;
30. N-{1-[(E)-3-(4-Nitro-phenyl)-allyl]-4-oxo-3,4-dihydro-phthalazin-6-yl}-3,4-dimethoxy-benzamide;
31. N-{1-[(E)-3-(4-Nitro-phenyl)-allyl]-4-oxo-3,4-dihydro-phthalazin-6-yl}-3-cyclopentyl-propionamide;
32. 2-Propyl-pentanoic acid {1-[(E)-3-(4-nitro-phenyl)-allyl]-4-oxo-3,4-dihydro-phthalazin-6-yl}-amide;
33. 1-{1-[(E)-3-(4-Nitro-phenyl)-allyl]-4-oxo-3,4-dihydro-phthalazin-6-yl}-3-(3-trifluoromethyl-phenyl)-urea;
34. 1-{1-[(E)-3-(4-Nitro-phenyl)-allyl]-4-oxo-3,4-dihydro-phthalazin-6-yl}-(3-methoxy-phenyl)-urea;
35. 1-{1-[(E)-3-(4-Nitro-phenyl)-allyl]-4-oxo-3,4-dihydro-phthalazin-6-yl}-3-p-tolyl-urea;
36. 1-{1-[(E)-3-(4-Nitro-phenyl)-allyl]-4-oxo-3,4-dihydro-phthalazin-6-yl}-3-(2,4-difluoro-phenyl)-urea;
37. 1-{1-[(E)-3-(4-Nitro-phenyl)-allyl]-4-oxo-3,4-dihydro-phthalazin-6-yl}-3-(3,4-dichloro-phenyl)-urea;
38. 1-{1-[(E)-3-(4-Nitro-phenyl)-allyl]-4-oxo-3,4-dihydro-phthalazin-6-yl}-3-pyridin-3-yl-urea;
39. 7-Amino-4-[(E)-3-(4-nitro-phenyl)-allyl]-2H-phthalazin-1-one;

40. N-(4-Oxo-1-thiophen-3-ylmethyl-3,4-dihydro-phthalazin-6-yl)-propionamide;
41. N-(4-Oxo-1-thiophen-3-ylmethyl-3,4-dihydro-phthalazin-6-yl)-4-trifluoromethyl-benzamide;
42. Furan-2-carboxylic acid (4-oxo-1-thiophen-3-ylmethyl-3,4-dihydro-phthalazin-6-yl)-amide;
43. N-(4-Oxo-1-thiophen-3-ylmethyl-3,4-dihydro-phthalazin-6-yl)-3,4-dimethoxy-benzamide;
44. N-(4-Oxo-1-thiophen-3-ylmethyl-3,4-dihydro-phthalazin-6-yl)-3-cyclopentyl-propionamide;
45. 2-Propyl-pentanoic acid (4-oxo-1-thiophen-3-ylmethyl-3,4-dihydro-phthalazin-6-yl)-amide;
46. 1-(4-Oxo-1-thiophen-3-ylmethyl-3,4-dihydro-phthalazin-6-yl)-3-(3-trifluoromethyl-phenyl)-urea;
47. 1-(4-Oxo-1-thiophen-3-ylmethyl-3,4-dihydro-phthalazin-6-yl)-(3-methoxy-phenyl)-urea;
48. 1-(4-Oxo-1-thiophen-3-ylmethyl-3,4-dihydro-phthalazin-6-yl)-3-p-tolyl-urea;
49. 1-(4-Oxo-1-thiophen-3-ylmethyl-3,4-dihydro-phthalazin-6-yl)-3-(2,4-difluoro-phenyl)-urea;
50. 1-(4-Oxo-1-thiophen-3-ylmethyl-3,4-dihydro-phthalazin-6-yl)-3-(3,4-dichloro-phenyl)-urea;
51. 1-(4-Oxo-1-thiophen-3-ylmethyl-3,4-dihydro-phthalazin-6-yl)-3-pyridin-3-yl-urea;
52. 7-Amino-4-thiophen-3-ylmethyl-2H-phthalazin-1-one;
53. N-[1-(3-Methoxy-benzyl)-4-oxo-3,4-dihydro-phthalazin-6-yl]-propionamide;
54. N-[1-(3-Methoxy-benzyl)-4-oxo-3,4-dihydro-phthalazin-6-yl]-4-trifluoromethyl-benzamide;
55. Furan-2-carboxylic acid [1-(3-methoxy-benzyl)-4-oxo-3,4-dihydro-phthalazin-6-yl]-amide;
56. N-[1-(3-Methoxy-benzyl)-4-oxo-3,4-dihydro-phthalazin-6-yl]-3,4-dimethoxy-benzamide;
57. N-[1-(3-Methoxy-benzyl)-4-oxo-3,4-dihydro-phthalazin-6-yl]-3-cyclopentyl-propionamide;
58. 2-Propyl-pentanoic acid [1-(3-methoxy-benzyl)-4-oxo-3,4-dihydro-phthalazin-6-yl]-amide;
59. 1-[1-(3-Methoxy-benzyl)-4-oxo-3,4-dihydro-phthalazin-6-yl]-3-(3-trifluoromethyl-phenyl)-urea;
60. 1-[1-(3-Methoxy-benzyl)-4-oxo-3,4-dihydro-phthalazin-6-yl]-(3-methoxy-phenyl)-urea;
61. 1-[1-(3-Methoxy-benzyl)-4-oxo-3,4-dihydro-phthalazin-6-yl]-3-p-tolyl-urea;
62. 1-[1-(3-Methoxy-benzyl)-4-oxo-3,4-dihydro-phthalazin-6-yl]-3-(2,4-difluoro-phenyl)-urea;
63. 1-[1-(3-Methoxy-benzyl)-4-oxo-3,4-dihydro-phthalazin-6-yl]-3-(3,4-dichloro-phenyl)-urea;
64. 1-[1-(3-Methoxy-benzyl)-4-oxo-3,4-dihydro-phthalazin-6-yl]-3-pyridin-3-yl-urea;
65. 7-Amino-4-(3-methoxy-benzyl)-2H-phthalazin-1-one;
66. N-(4-Oxo-1-propyl-3,4-dihydro-phthalazin-6-yl)-propionamide;
67. N-(4-Oxo-1-propyl-3,4-dihydro-phthalazin-6-yl)-4-trifluoromethyl-benzamide;
68. Furan-2-carboxylic acid (4-oxo-1-propyl-3,4-dihydro-phthalazin-6-yl)-amide;
69. N-(4-Oxo-1-propyl-3,4-dihydro-phthalazin-6-yl)-3,4-dimethoxy-benzamide;
70. N-(4-Oxo-1-propyl-3,4-dihydro-phthalazin-6-yl)-3-cyclopentyl-propionamide;
71. 2-Propyl-pentanoic acid (4-oxo-1-propyl-3,4-dihydro-phthalazin-6-yl)-amide;
72. 1-(4-Oxo-1-propyl-3,4-dihydro-phthalazin-6-yl)-3-(3-trifluoromethyl-phenyl)-urea;
73. 1-(4-Oxo-1-propyl-3,4-dihydro-phthalazin-6-yl)-(3-methoxy-phenyl)-urea;
74. 1-(4-Oxo-1-propyl-3,4-dihydro-phthalazin-6-yl)-3-p-tolyl-urea;
75. 1-(4-Oxo-1-propyl-3,4-dihydro-phthalazin-6-yl)-3-(2,4-difluoro-phenyl)-urea;
76. 1-(4-Oxo-1-propyl-3,4-dihydro-phthalazin-6-yl)-3-(3,4-dichloro-phenyl)-urea;
77. 1-(4-Oxo-1-propyl-3,4-dihydro-phthalazin-6-yl)-3-pyridin-3-yl-urea;
78. 7-Amino-4-propyl-2H-phthalazin-1-one;
79. N-[1-(3,3-Dimethyl-butyl)-4-oxo-3,4-dihydro-phthalazin-6-yl]-propionamide;
80. N-[1-(3,3-Dimethyl-butyl)-4-oxo-3,4-dihydro-phthalazin-6-yl]-4-trifluoromethyl-benzamide;
81. Furan-2-carboxylic acid [1-(3,3-dimethyl-butyl)-4-oxo-3,4-dihydro-phthalazin-6-yl]-amide;
82. N-[1-(3,3-Dimethyl-butyl)-4-oxo-3,4-dihydro-phthalazin-6-yl]-3,4-dimethoxy-benzamide;
83. N-[1-(3,3-Dimethyl-butyl)-4-oxo-3,4-dihydro-phthalazin-6-yl]-3-cyclopentyl-propionamide;
84. 2-Propyl-pentanoic acid [1-(3,3-dimethyl-butyl)-4-oxo-3,4-dihydro-phthalazin-6-yl]-amide;
85. 1-[1-(3,3-Dimethyl-butyl)-4-oxo-3,4-dihydro-phthalazin-6-yl]-3-(3-trifluoromethyl-phenyl)-urea;
86. 1-[1-(3,3-Dimethyl-butyl)-4-oxo-3,4-dihydro-phthalazin-6-yl]-(3-methoxy-phenyl)-urea;
87. 1-[1-(3,3-Dimethyl-butyl)-4-oxo-3,4-dihydro-phthalazin-6-yl]-3-p-tolyl-urea;
88. 1-[1-(3,3-Dimethyl-butyl)-4-oxo-3,4-dihydro-phthalazin-6-yl]-3-(2,4-difluoro-phenyl)-urea;
89. 1-[1-(3,3-Dimethyl-butyl)-4-oxo-3,4-dihydro-phthalazin-6-yl]-3-(3,4-dichloro-phenyl)-urea;
90. 1-[1-(3,3-Dimethyl-butyl)-4-oxo-3,4-dihydro-phthalazin-6-yl]-3-pyridin-3-yl-urea;
91. 7-Amino-4-(3,3-dimethyl-butyl)-2H-phthalazin-1-one;
92. N-[4-Oxo-1-(3-phenyl-propyl)-3,4-dihydro-phthalazin-6-yl]-propionamide;
93. N-[4-Oxo-1-(3-phenyl-propyl)-3,4-dihydro-phthalazin-6-yl]-4-trifluoromethyl-benzamide;
94. Furan-2-carboxylic acid [4-oxo-1-(3-phenyl-propyl)-3,4-dihydro-phthalazin-6-yl]-amide;
95. N-[4-Oxo-1-(3-phenyl-propyl)-3,4-dihydro-phthalazin-6-yl]-3,4-dimethoxy-benzamide;
96. N-[4-Oxo-1-(3-phenyl-propyl)-3,4-dihydro-phthalazin-6-yl]-3-cyclopentyl-propionamide;
97. 2-Propyl-pentanoic acid [4-oxo-1-(3-phenyl-propyl)-3,4-dihydro-phthalazin-6-yl]-amide;
98. 1-[4-Oxo-1-(3-phenyl-propyl)-3,4-dihydro-phthalazin-6-yl]-3-(3-trifluoromethyl-phenyl)-urea;
99. 1-[4-Oxo-1-(3-phenyl-propyl)-3,4-dihydro-phthalazin-6-yl]-(3-methoxy-phenyl)-urea;
100. 1-[4-Oxo-1-(3-phenyl-propyl)-3,4-dihydro-phthalazin-6-yl]-3-p-tolyl-urea;
101. 1-[4-Oxo-1-(3-phenyl-propyl)-3,4-dihydro-phthalazin-6-yl]-3-(2,4-difluoro-phenyl)-urea;
102. 1-[4-Oxo-1-(3-phenyl-propyl)-3,4-dihydro-phthalazin-6-yl]-3-(3,4-dichloro-phenyl)-urea;
103. 1-[4-Oxo-1-(3-phenyl-propyl)-3,4-dihydro-phthalazin-6-yl]-3-pyridin-3-yl-urea;
104. 7-Amino-4-(3-phenyl-propyl)-2H-phthalazin-1-one;
105. N-(4-Oxo-1-pyridin-3-ylmethyl-3,4-dihydro-phthalazin-6-yl)-propionamide;
106. N-(4-Oxo-1-pyridin-3-ylmethyl-3,4-dihydro-phthalazin-6-yl)-4-trifluoromethyl-benzamide;
107. Furan-2-carboxylic acid (4-oxo-1-pyridin-3-ylmethyl-3,4-dihydro-phthalazin-6-yl)-amide;
108. N-(4-Oxo-1-pyridin-3-ylmethyl-3,4-dihydro-phthalazin-6-yl)-succinamic acid ethyl ester;

109. N-(4-Oxo-1-pyridin-3-ylmethyl-3,4-dihydro-phthalazin-6-yl)-3-cyclopentyl-propionamide;
110. 2-Propyl-pentanoic acid (4-oxo-1-pyridin-3-ylmethyl-3,4-dihydro-phthalazin-6-yl)-amide;
111. 1-(4-Oxo-1-pyridin-3-ylmethyl-3,4-dihydro-phthalazin-6-yl)-3-(3-trifluoromethyl-phenyl)-urea;
112. 1-(3-Methoxy-phenyl)-3-(4-oxo-1-pyridin-3-ylmethyl-3,4-dihydro-phthalazin-6-yl)-urea;
113. 1-(4-Oxo-1-pyridin-3-ylmethyl-3,4-dihydro-phthalazin-6-yl)-3-p-tolyl-urea;
114. 1-(2,4-Difluoro-phenyl)-3-(4-oxo-1-pyridin-3-ylmethyl-3,4-dihydro-phthalazin-6-yl)-urea;
115. 1-(3,4-Dichloro-phenyl)-3-(4-oxo-1-pyridin-3-ylmethyl-3,4-dihydro-phthalazin-6-yl)-urea;
116. 1-(4-Oxo-1-pyridin-3-ylmethyl-3,4-dihydro-phthalazin-6-yl)-3-pyridin-3-yl-urea;
117. 7-Amino-4-pyridin-3-ylmethyl-2H-phthalazin-1-one
118. N-(4-Oxo-1-pyridin-3-ylmethyl-3,4-dihydro-phthalazin-6-yl)-benzamide;
119. N-[1-(4-Chloro-benzyl)-4-oxo-3,4-dihydro-phthalazin-6-yl]-propionamide;
120. N-[1-(4-Chloro-benzyl)-4-oxo-3,4-dihydro-phthalazin-6-yl]-4-trifluoromethyl-benzamide;
121. Furan-2-carboxylic acid [1-(4-chloro-benzyl)-4-oxo-3,4-dihydro-phthalazin-6-yl]-amide;
122. N-[1-(4-Chloro-benzyl)-4-oxo-3,4-dihydro-phthalazin-6-yl]-succinamic acid ethyl ester;
123. N-[1-(4-Chloro-benzyl)-4-oxo-3,4-dihydro-phthalazin-6-yl]-3-cyclopentyl-propionamide;
124. 2-Propyl-pentanoic acid [1-(4-chloro-benzyl)-4-oxo-3,4-dihydro-phthalazin-6-yl]-amide;
125. 1-[1-(4-Chloro-benzyl)-4-oxo-3,4-dihydro-phthalazin-6-yl]-3-(3-trifluoromethyl-phenyl)-urea;
126. 1-[1-(4-Chloro-benzyl)-4-oxo-3,4-dihydro-phthalazin-6-yl]-3-(3-methoxy-phenyl)-urea;
127. 1-[1-(4-Chloro-benzyl)-4-oxo-3,4-dihydro-phthalazin-6-yl]-3-p-tolyl-urea;
128. 1-[1-(4-Chloro-benzyl)-4-oxo-3,4-dihydro-phthalazin-6-yl]-3-(2,4-difluoro-phenyl)-urea;
129. 1-[1-(4-Chloro-benzyl)-4-oxo-3,4-dihydro-phthalazin-6-yl]-3-(3,4-dichloro-phenyl)-urea;
130. 1-[1-[4-Chloro-benzyl)-4-oxo-3,4-dihydro-phthalazin-6-yl]-3-pyridin-3-yl-urea;
131. 7-Amino-4-(4-Chloro-benzyl)-2H-phthalazin-1-one;
132. N-[1-(4-Cyano-benzyl)-4-oxo-3,4-dihydro-phthalazin-6-yl]-propionamide;
133. N-[1-(4-Cyano-benzyl)-4-oxo-3,4-dihydro-phthalazin-6-yl]-4-trifluoromethyl-benzamide;
134. Furan-2-carboxylic acid [1-(4-cyano-benzyl)-4-oxo-3,4-dihydro-phthalazin-6-yl]-amide;
135. N-[1-(4-Cyano-benzyl)-4-oxo-3,4-dihydro-phthalazin-6-yl]-succinamic acid ethyl ester;
136. N-[1-(4-Cyano-benzyl)-4-oxo-3,4-dihydro-phthalazin-6-yl]-3-cyclopentyl-propionamide;
137. 2-Propyl-pentanoic acid [1-(4-cyano-benzyl)-4-oxo-3,4-dihydro-phthalazin-6-yl]-amide;
138. 1-[1-(4-Cyano-benzyl)-4-oxo-3,4-dihydro-phthalazin-6-yl]-3-(3-trifluoromethyl-phenyl)-urea;
139. 1-[1-(4-Cyano-benzyl)-4-oxo-3,4-dihydro-phthalazin-6-yl]-3-(3-methoxy-phenyl)-urea;
140. 1-[1-(4-Cyano-benzyl)-4-oxo-3,4-dihydro-phthalazin-6-yl]-3-p-tolyl-urea;
141. 1-[1-(4-Cyano-benzyl)-4-oxo-3,4-dihydro-phthalazin-6-yl]-3-(2,4-difluoro-phenyl)-urea;
142. 1-[1-(4-Cyano-benzyl)-4-oxo-3,4-dihydro-phthalazin-6-yl]-3-(3,4-dichloro-phenyl)-urea;
143. 1-[1-(4-Cyano-benzyl)-4-oxo-3,4-dihydro-phthalazin-6-yl]-3-pyridin-3-yl-urea;
144. 7-Amino-4-(4-Cyano-benzyl)-2H-phthalazin-1-one;
145. N-[1-(3-Fluoro-benzyl)-4-oxo-3,4-dihydro-phthalazin-6-yl]-propionamide;
146. N-[1-(3-Fluoro-benzyl)-4-oxo-3,4-dihydro-phthalazin-6-yl]-4-trifluoromethyl-benzamide;
147. Furan-2-carboxylic acid [1-(3-fluoro-benzyl)-4-oxo-3,4-dihydro-phthalazin-6-yl]-amide;
148. N-[1-(3-Fluoro-benzyl)-4-oxo-3,4-dihydro-phthalazin-6-yl]-succinamic acid ethyl ester;
149. N-[1-(3-Fluoro-benzyl)-4-oxo-3,4-dihydro-phthalazin-6-yl]-3-cyclopentyl-propionamide;
150. 2-Propyl-pentanoic acid [1-(3-fluoro-benzyl)-4-oxo-3,4-dihydro-phthalazin-6-yl]-amide;
151. 1-[1-(3-Fluoro-benzyl)-4-oxo-3,4-dihydro-phthalazin-6-yl]-3-(3-trifluoromethyl-phenyl)-urea;
152. 1-[1-(3-Fluoro-benzyl)-4-oxo-3,4-dihydro-phthalazin-6-yl]-3-(3-methoxy-phenyl)-urea;
153. 1-[1-(3-Fluoro-benzyl)-4-oxo-3,4-dihydro-phthalazin-6-yl]-3-p-tolyl-urea;
154. 1-[1-(3-Fluoro-benzyl)-4-oxo-3,4-dihydro-phthalazin-6-yl]-3-(2,4-difluoro-phenyl)-urea;
155. 1-[1-(3-Fluoro-benzyl)-4-oxo-3,4-dihydro-phthalazin-6-yl]-3-(3,4-dichloro-phenyl)-urea;
156. 1-[1-(3-Fluoro-benzyl)-4-oxo-3,4-dihydro-phthalazin-6-yl]-3-pyridin-3-yl-urea;
157. 7-Amino-4-(3-Fluoro-benzyl)-2H-phthalazin-1-one;
158. N-[1-(3-Methyl-benzyl)-4-oxo-3,4-dihydro-phthalazin-6-yl]-propionamide;
159. N-[1-(3-Methyl-benzyl)-4-oxo-3,4-dihydro-phthalazin-6-yl]-4-trifluoromethyl-benzamide;
160. Furan-2-carboxylic acid [1-(3-methyl-benzyl)-4-oxo-3,4-dihydro-phthalazin-6-yl]-amide;
161. N-[1-(3-Methyl-benzyl)-4-oxo-3,4-dihydro-phthalazin-6-yl]-succinamic acid ethyl ester;
162. N-[1-(3-Methyl-benzyl)-4-oxo-3,4-dihydro-phthalazin-6-yl]-3-cyclopentyl-propionamide;
163. 2-Propyl-pentanoic acid [1-(3-methyl-benzyl)-4-oxo-3,4-dihydro-phthalazin-6-yl]-amide;
164. 1-[1-(3-Methyl-benzyl)-4-oxo-3,4-dihydro-phthalazin-6-yl]-3-(3-trifluoromethyl-phenyl)-urea;
165. 1-[1-(3-Methyl-benzyl)-4-oxo-3,4-dihydro-phthalazin-6-yl]-3-(3-methoxy-phenyl)-urea;
166. 1-[1-(3-Methyl-benzyl)-4-oxo-3,4-dihydro-phthalazin-6-yl]-3-p-tolyl-urea;
167. 1-[1-(3-Methyl-benzyl)-4-oxo-3,4-dihydro-phthalazin-6-yl]-3-(2,4-difluoro-phenyl)-urea;
168. 1-[1-(3-Methyl-benzyl)-4-oxo-3,4-dihydro-phthalazin-6-yl]-3-(3,4-dichloro-phenyl)-urea;
169. 1-[1-(3-Methyl-benzyl)-4-oxo-3,4-dihydro-phthalazin-6-yl]-3-pyridin-3-yl-urea;
170. 7-Amino-4-(3-Methyl-benzyl)-2H-phthalazin-1-one;
171. N-[1-(2,4-Dichloro-benzyl)-4-oxo-3,4-dihydro-phthalazin-6-yl]-propionamide;
172. N-[1-(2,4-Dichloro-benzyl)-4-oxo-3,4-dihydro-phthalazin-6-yl]-4-trifluoromethyl-benzamide;
173. Furan-2-carboxylic acid [1-(2,4-dichloro-benzyl)-4-oxo-3,4-dihydro-phthalazin-6-yl]-amide;
174. N-[1-(2,4-Dichloro-benzyl)-4-oxo-3,4-dihydro-phthalazin-6-yl]-succinamic acid ethyl ester;
175. N-[1-(2,4-Dichloro-benzyl)-4-oxo-3,4-dihydro-phthalazin-6-yl]-3-cyclopentyl-propionamide;
176. 2-Propyl-pentanoic acid [1-(2,4-dichloro-benzyl)-4-oxo-3,4-dihydro-phthalazin-6-yl]-amide;
177. 1-[1-(2,4-Dichloro-benzyl)-4-oxo-3,4-dihydro-phthalazin-6-yl]-3-(3-trifluoromethyl-phenyl)-urea;

178. 1-[1-(2,4-Dichloro-benzyl)-4-oxo-3,4-dihydro-phthalazin-6-yl]-3-(3-methoxy-phenyl)-urea;
179. 1-[1-(2,4-Dichloro-benzyl)-4-oxo-3,4-dihydro-phthalazin-6-yl]-3-p-tolyl-urea;
180. 1-[1-(2,4-Dichloro-benzyl)-4-oxo-3,4-dihydro-phthalazin-6-yl]-3-(2,4-difluoro-phenyl)-urea;
181. 1-[1-(2,4-Dichloro-benzyl)-4-oxo-3,4-dihydro-phthalazin-6-yl]-3-(3,4-dichloro-phenyl)-urea;
182. 1-[1-(2,4-Dichloro-benzyl)-4-oxo-3,4-dihydro-phthalazin-6-yl]-3-pyridin-3-yl-urea;
183. 7-Amino-4-(2,4-dichloro-benzyl)-2H-phthalazin-1-one;
184. N-(4-Oxo-1-quinolin-3-ylmethyl-3,4-dihydro-phthalazin-6-yl)-propionamide;
185. N-(4-Oxo-1-quinolin-3-ylmethyl-3,4-dihydro-phthalazin-6-yl)-4-trifluoromethyl-benzamide;
186. Furan-2-carboxylic acid (4-oxo-1-quinolin-3-ylmethyl-3,4-dihydro-phthalazin-6-yl)-amide;
187. N-(4-Oxo-1-quinolin-3-ylmethyl-3,4-dihydro-phthalazin-6-yl)-succinamic acid ethyl ester;
188. N-(4-Oxo-1-quinolin-3-ylmethyl-3,4-dihydro-phthalazin-6-yl)-3-cyclopentyl-propionamide;
189. 2-Propyl-pentanoic acid (4-oxo-1-quinolin-3-ylmethyl-3,4-dihydro-phthalazin-6-yl)-amide;
190. 1-(4-Oxo-1-quinolin-3-ylmethyl-3,4-dihydro-phthalazin-6-yl)-3-(3-trifluoromethyl-phenyl)-urea;
191. 1-(4-Oxo-1-quinolin-3-ylmethyl-3,4-dihydro-phthalazin-6-yl)-3-(3-methoxy-phenyl)-urea;
192. 1-(4-Oxo-1-quinolin-3-ylmethyl-3,4-dihydro-phthalazin-6-yl)-3-p-tolyl-urea;
193. 1-(4-Oxo-1-quinolin-3-ylmethyl-3,4-dihydro-phthalazin-6-yl)-3-(2,4-difluoro-phenyl)-urea;
194. 1-(4-Oxo-1-quinolin-3-ylmethyl-3,4-dihydro-phthalazin-6-yl)-3-(3,4-dichloro-phenyl)-urea;
195. 1-(4-Oxo-1-quinolin-3-ylmethyl-3,4-dihydro-phthalazin-6-yl)-3-pyridin-3-yl-urea;
196. 7-Amino-4-quinolin-3-ylmethyl-2H-phthalazin-1-one;
197. N-[4-Oxo-1-(2-trifluoromethyl-benzyl)-3,4-dihydro-phthalazin-6-yl]-propionamide;
198. N-[4-Oxo-1-(2-trifluoromethyl-benzyl)-3,4-dihydro-phthalazin-6-yl]-4-trifluoromethyl-benzamide;
199. Furan-2-carboxylic acid [4-oxo-1-(2-trifluoromethyl-benzyl)-3,4-dihydro-phthalazin-6-yl]-amide;
200. N-[4-Oxo-1-(2-trifluoromethyl-benzyl)-3,4-dihydro-phthalazin-6-yl]-succinamic acid ethyl ester;
201. N-[4-Oxo-1-(2-trifluoromethyl-benzyl)-3,4-dihydro-phthalazin-6-yl]-3-cyclopentyl-propionamide;
202. 2-Propyl-pentanoic acid [4-oxo-1-(2-trifluoromethyl-benzyl)-3,4-dihydro-phthalazin-6-yl]-amide;
203. 1-[4-Oxo-1-(2-trifluoromethyl-benzyl)-3,4-dihydro-phthalazin-6-yl]-3-(3-trifluoromethyl-phenyl)-urea;
204. 1-[4-Oxo-1-(2-trifluoromethyl-benzyl)-3,4-dihydro-phthalazin-6-yl]-3-(3-methoxy-phenyl)-urea;
205. 1-[4-Oxo-1-(2-trifluoromethyl-benzyl)-3,4-dihydro-phthalazin-6-yl]-3-p-tolyl-urea;
206. 1-[4-Oxo-1-(2-trifluoromethyl-benzyl)-3,4-dihydro-phthalazin-6-yl]-3-(2,4-difluoro-phenyl)-urea;
207. 1-[4-Oxo-1-(2-trifluoromethyl-benzyl)-3,4-dihydro-phthalazin-6-yl]-3-(3,4-dichloro-phenyl)-urea;
208. 1-[4-Oxo-1-(2-trifluoromethyl-benzyl)-3,4-dihydro-phthalazin-6-yl]-3-pyridin-3-yl-urea;
209. 7-Amino-4-(2-trifluoromethyl-benzyl)-2H-phthalazin-1-one.

As set forth above, the process for preparing the amino-phthalazinone derivatives of formula (I) represents a further object of the present invention.

The compounds of formula (I) and the pharmaceutically acceptable salts thereof, may be thus obtained by a process comprising:
a) reacting a compound of formula (II)

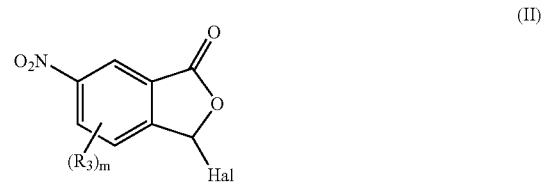

wherein $R_3$ and m have the above reported meanings and Hal represents a halogen atom, with a suitable phosphine derivative ($PL_3$), under optional reductive conditions, so as to obtain a compound of formula (III)

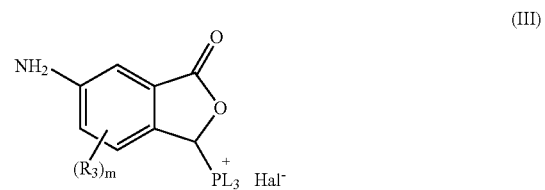

wherein P is a phosphorous atom and L are the phosphine ligands;
b) reacting the compound of formula (III) with an aldehydic Resin-CHO, in the presence of a suitable reducing agent, so as to obtain a resin supported compound of formula (IV)

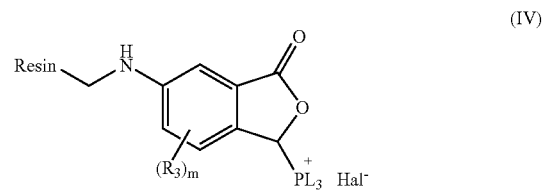

wherein $R_3$, m, P, L, Hal and the Resin are as above defined;
c) reacting the compound of formula (IV) with a carbonyl derivative of formula (V) or a nitroso derivative of formula (VI)

$$R_4\text{—}CO\text{—}R_5 \quad (V)$$

$$R'\text{—}NO \quad (VI)$$

wherein $R_4$, $R_5$ and R' are as above defined; so as to obtain the compound of formula (VII)

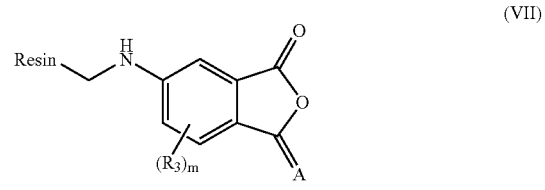

wherein A is a group $=CR_4R_5$ or $=NR'$, respectively; and optionally reacting the compound of formula (VII) according to any one of the alternative steps d.1) or d.2) below d.1) with one of the derivatives of formula (VIII), (IX), (X) or (XI), under optional basic conditions,

R'COZ (VIII),

R'NCO (IX),

R'OCOZ (X),

R'SO$_2$Z (XI)

wherein Z is a halogen atom or a suitable leaving group and R' is as above defined, so as to obtain the compound of formula (XII)

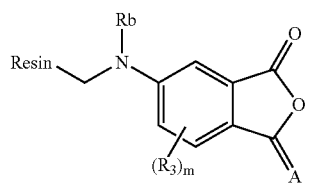

(XII)

wherein Rb is —COR', —CONHR', —COOR' or —SO$_2$R', respectively; or d.2) with a compound of formula (XIII)

Rb-Z (XIII)

wherein Z is a halogen atom and Rb is alkyl, cycloalkyl, cycloalkylalkyl, aryl, arylalkyl, heterocyclyl or heterocyclylalkyl as above defined, so as to obtain the corresponding compound of the above formula (XII);

e) reacting the thus obtained compounds of formula (VII) or (XII) with a hydrazine derivative of formula (XIV)

R$_2$—NH—NH$_2$ (XIV)

wherein R$_2$ is as above defined, so as to obtain the compounds of formula (XV) or (XVI), respectively

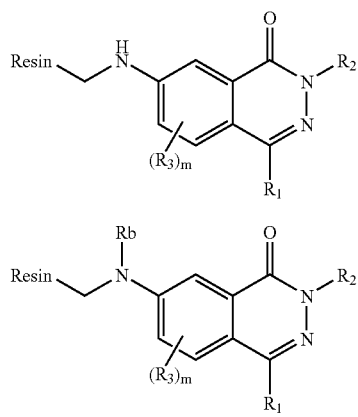

wherein Rb, R$_2$, R$_3$, m and the Resin are as above defined and R$_1$ is a group of formula —CHR$_4$R$_5$ or —NHR' wherein R$_4$, R$_5$ and R' are as above defined;

f) reacting the compounds of formula (XV) or (XVI) under acidic conditions so as to obtain the compound of formula (I) and, whenever desired, converting it into another compound of formula (I) and/or into a pharmaceutically acceptable salt thereof.

The above process is an analogy process which can be carried out according to well known methods.

It is clear to the person skilled in the art that if a compound of formula (I), prepared according to the above process, is obtained as an admixture of isomers, their separation into the single isomers of formula (I), carried out according to conventional techniques, is still within the scope of the present invention.

Likewise, the conversion into the free compound (I) of a corresponding salt thereof, according to well-known procedures in the art, is still within the scope of the invention.

According to step a) of the process, a compound of formula (II) wherein Hal represents a halogen atom, preferably bromine, is reacted with a suitable phosphine derivative PL$_3$ such as, for instance, triphenylphosphine, tri-n-butylphoshine, tri-t-butylphosphine or 1,4-bis(diphenylphosphino)butane.

Preferably, the phosphine derivative is triphenylphosphine PPh$_3$.

The reaction may be carried out in a variety of solvents for instance comprising ethyl acetate, ethyl propionate and the like, dimethylformammide, dimethylacetammide and the like, dichloromethane chloroform and the like, acetone, or acetonitrile; preferred is the use of ethyl propionate. The temperature may vary from about 20° C. to about 100° C.

The reaction may be performed by adding the phosphine to a solution of the compound of formula (II) or by adding a solution of (II) to the phosphine.

When using triphenylphosphine, the compound of formula (II) is directly converted into the corresponding derivative of formula (III) bearing the amino group in place of the original nitro group. Alternatively, when using PL$_3$ reagents other than triphenylphosphine, the compound of formula (II) may be first converted into an intermediate derivative of formula (IIa)

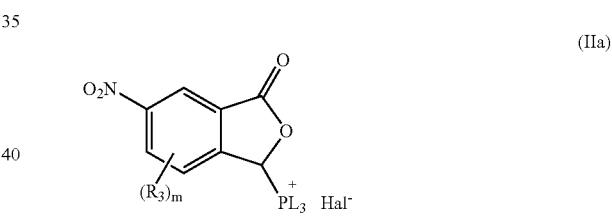

(IIa)

wherein R$_3$, m, P and L are as above defined, which has to be properly reduced to the compound of formula (III).

The reductive conditions to be employed are those conventionally used for reducing aromatic nitro derivatives to amino derivatives and comprise the use of chemical reducing agents such as, for instance, tin dichloride, iron and acetic acid, zinc and hydrochloric acid, or titanium trichloride.

Alternatively, the reductive step may occur under catalytic hydrogenation conditions in the presence of suitable catalysts, typically platinum, palladium or palladium on charcoal.

Preferably, the compound of formula (II) is conveniently converted into the compound of formula (III) by using triphenylphosphine.

According to step b) of the process, the compound of formula (III) is reacted, in the presence of a reducing agent such as, for instance, a pyridine-borane complex, sodium cyanoboron hydride, sodium triacetoxy boron hydride, dimethylsufide borane and the like, with a suitable aldehydic RCHO resin, for instance a polystirene or polyethyleneglycol resin.

Preferably, the resin is a 4-(4-formyl-3-methoxyphenoxy) butyryl aminomethylated resin or 4-(4-formyl-3-methoxyphenoxy)butyryl (NOVAGEL™).

The reaction is carried out in the presence of a suitable solvent, preferably dichloromethane, 2,2,2-trifluoroethanol and acetic acid, by adding an excess of the reducing agent, optionally dissolved into the same solvent, directly to the mixture of resin and of the compound of formula (III), and by stirring at a temperature ranging from about 0° C. to about 40° C. for a suitable time. As an example, the reaction may be carried at about 20° C. for about 15 hours.

According to step c) of the process, the compound of formula (IV) is then reacted with a compound of formula (V) or, alternatively, of formula (VI), so as to obtain the corresponding derivative of formula (VII).

The reaction is carried out in the presence of a suitable base, for instance triethylamine, diisopropylethylamine, piperidine, sodium carbonate, cesium carbonate, potassium t-butoxide, sodium methoxide, diazabicycloundecene, potassium hydroxide and the like, optionally in the presence of a suitable phase-transfer catalyst.

The compound of formula (V) or, alternatively, of formula (VI), is added to a suspension of the compound of formula (IV) in a suitable solvent such as dichloromethane, dimethyl formammide, tetrahydrofuran or the like. The temperature is then brought to a suitable value, for instance from about −70° C. to about 40° C. according to the electrophile (V) or (VI), and the base is added. Stirring is carried on for a suitable time, for instance from about 2 to about 15 hours.

The product of formula (VII) thus obtained may be further reacted according to any one of the alternative steps d.1) or d.2), or directly processed according to step e).

According to step d.1) of the process, in particular, the compound of formula (VII) is reacted with a carboxylic acid derivative of formula (VIII), with an isocyanate of formula (IX), with a chloroformate derivative of formula (X) or with a sulphonyl derivative of formula (XI), so as to obtain the corresponding compound of formula (XII) wherein Rb is a group of formula —COR', —CONHR', —COOR' or —SO$_2$R', respectively.

When using a compound of formula (VIII), (X) or (XI), Z is preferably a halogen atom and, even more preferably, a chlorine atom. In this instance, the compound of formula (VII) is suspended into a suitable solvent such as dichloromethane, dimethylformammide, tetrahydrofuran, dioxane or the like, and a suitable base is then added, for instance triethylamine, diisopropylethylamine, sodium carbonate or the like. The electrophile of general formula (VIII), (X), or (XI) is then added and the mixture stirred for about 2 to about 15 hours, at a temperature ranging from about 20° C. to about 80° C. When using an isocyanate of general formula (IX), the reaction conditions are the same as above reported except that the base may not be required. In the latter case a catalyst such as dimethylamino pyridine may be optionally used.

Substantially analogous considerations apply when considering step d.2) of the process wherein the compound of formula (VII) is further converted into the corresponding functionalized amino derivative of formula (XII), according to well known methods.

As an example, the compound of formula (VII) may be reacted with a derivative of formula (XIII) wherein Z is halogen, for instance bromine, and Rb is an arylalkyl group such as, for instance, the benzyl group, by working according to conventional methods.

According to step e) of the process, the compound of formula (VII) obtained from step c) or, alternatively, the compound of formula (XII) obtained from any one of steps d.1) or d.2), is reacted with hydrazine or a hydrazine derivative of formula (XIV) so as to obtain the corresponding compounds of formula (XV) or (XVI).

The compound of formula (XII) is suspended in a suitable solvent, preferably dimethylformammide, in the presence of hydrazine hydrate or another hydrazine of general formula (XIV) and stirred at a suitable temperature, for instance at 20° C., for about 2 to about 20 hours.

According to step f) of the process, the compounds of formula (XV) or (XVI) are reacted under acidic conditions, preferably in the presence of trifluoroacetic acid, so as to yield the desired compound of formula (I). Compounds of formula (XV) or (XVI) may be thus suspended in a solution of 5-95% trifluoroacetic acid in dichloromethane and the mixture stirred at a temperture ranging from about 20° C. to refluxing temperature, for a time varying from about 5 minutes to about 3 hours.

From the above, it is clear to the skilled man that by carrying out the above resin cleavage from the compound of formula (XV), the corresponding derivative having both Ra and Rb as hydrogen atoms will be obtained.

Likewise, when starting from the compound of formula (XVI), the corresponding derivative of formula (I) having one of Ra or Rb, e.g. Ra, as a hydrogen atom and the other, e.g. Rb, as a group as defined under steps d1) or d.2), will be obtained.

In addition, it is clear to the skilled man that, if desired, any of the above compounds of formula (I) may be further converted by working according to conventional methods into other compounds of formula (I), as set forth in step f).

As an example, the compounds of formula (I) wherein both Ra and Rb are other than hydrogen atoms may be prepared according to well-known methods by reacting any compound of formula (I) having one of Ra or Rb as a hydrogen atom, into another compound of formula (I) having this same hydrogen atom being replaced by a suitable group.

When preparing the compounds of formula (I) according to any variant of the process, which are all to be intended as within the scope of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

Pharmaceutically acceptable salts of the compounds of formula (I) or, alternatively, their free compounds from the salts thereof, my be all obtained according to conventional methods.

The compounds of formula (II) are known or easily prepared according to known methods [see, for a reference, *J. Org. Chem.* (1985), 50, 4120-4125; *J. Chem. Soc.* (1961), 5275-5284].

Alternatively, the compounds of formula (II) wherein Hal represents a bromine atom, may be prepared as reported in the working examples, that is by reacting commercially available 6-nitro-phthalide under brominating conditions, for instance with bromine in the presence of aqueous hydrogen peroxide, in a suitable solvent such as dichloromethane, dichloromethane/water or hexane/water admixtures, at a temperature varying from about 20° C. to reflux.

The compounds of formula (V), (VI), (VIII), (IX), (X), (XI), (XIII) and (XIV) are known or easily prepared according to well-known methods.

Likewise, the aldehydic resin R—CHO, the phosphine derivative PL$_3$ and any other suitable reagent of the process, are known compounds which are commercially available or easily prepared according to known methods.

The compounds of formula (I) of the invention were advantageously prepared according to combinatorial chemistry techniques widely known in the art, by accomplishing the aforementioned reactions between the several intermediates in a serial manner.

Therefore, all of the preferred compounds of the invention, whenever appropriate in the form of pharmaceutically acceptable salts, are herewith conveniently indicated and defined as products by process, that is as products of formula (I) which are obtainable, for instance through a defined process.

Therefore, herewith provided is any specific compound of formula (I) which is obtainable, for instance through a combinatorial chemistry technique according to the process of the invention, by first reacting the compound of formula (IV)

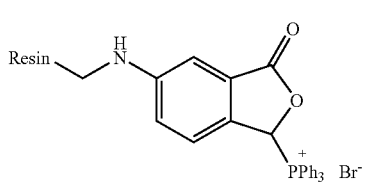

(IV)

with each one of the aldehyde derivatives of formula (V), as set forth in table I; by reacting any of the resultant compounds of formula (VII) with each one of the acyl chloride derivatives of formula (VIII), as set forth in table II; by reacting any of the resultant compounds of formula (XII) with hydrazine; and by working according to step f) of the process.

Also provided is any specific compound of formula (I) which is obtainable, for instance through a combinatorial chemistry technique according to the process of the invention, by first reacting the compound of formula (IV)

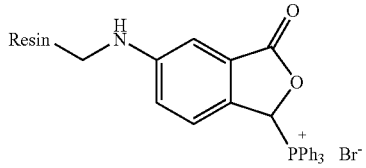

(IV)

with each one of the aldehyde derivatives of formula (V), as set forth in table I; by reacting any of the resultant compounds of formula (VII) with each one of the isocyanate derivatives of formula (IX), as set forth in table III; by reacting any of the resultant compounds of formula (XII) with hydrazine; and by working according to step f) of the process.

TABLE I

Aldehyde derivatives of formula (V) $R_4$—CO—$R_5$ ($R_5$ = H)

| | |
|---|---|
| 1. | 3,5-diiodo-4-hydroxybenzaldehyde |
| 2. | 3-iodobenzaldehyde |
| 3. | 3,5-dibromobenzaldehyde |
| 4. | 4-bromothiophene-2-carboxaldehyde |
| 5. | 2-naphthaldehyde |
| 6. | n-ethyl-carbazole-3-aldehyde |
| 7. | 4-chloro-1-methylpyrazole-3-carboxaldehyde |
| 8. | (3-formyl-1-phenyl-1h-pyrazol-5-yl)methyl acetate |
| 9. | 1-acetyl-3-indolecarboxaldehyde |
| 10. | methyl 4-formyl-1-methylpyrrole-2-carboxylate |
| 11. | 3,5-di-tert-butyl-4-hydroxybenzaldehyde |
| 12. | 5-(methylthio)-2-thiophenecarboxaldehyde |
| 13. | 4-(methylthio)benzaldehyde |

TABLE I-continued

Aldehyde derivatives of formula (V) $R_4$—CO—$R_5$ ($R_5$ = H)

| | |
|---|---|
| 14. | 3-nitro-4-(2-pyridylthio)benzaldehyde |
| 15. | 5-methyl-2-thiophenecarboxaldehyde |
| 16. | 3-acetoxybenzaldehyde |
| 17. | 3,4-dimethylbenzaldehyde |
| 18. | 4-pyridinecarboxaldehyde n-oxide |
| 19. | 4-fluoro-3-methylbenzaldehyde |
| 20. | 2,6-dichloroisonicotinaldehyde |
| 21. | 5-(2,4-difluorophenyl)-2-furaldehyde |
| 22. | 2-(4-bromobenzoyl)-1-benzofuran-5-carbaldehyde |
| 23. | 2-benzoyl-1-benzofuran-5-carbaldehyde |
| 24. | 2-butyl-4-formylimidazole |
| 25. | 5-benzyloxy-1h-pyrrolo[2,3-c]pyridine-3-carboxaldehyde |
| 26. | 6-methyl-2-pyridinecarboxaldehyde |
| 27. | 4-[4-(tert-butyl)thiazol-2-yl]benzaldehyde |
| 28. | 5-formyl-2,4-dimethoxy-pyrimidine |
| 29. | 2-[(4-chlorobenzyl)thio]pyrimidine-4-carbaldehyde |
| 30. | 3-fluoro-2-hydroxybenzaldehyde |
| 31. | 3-hydroxybenzaldehyde |
| 32. | 3-carboxybenzaldehyde |
| 33. | 4-vinylbenzaldehyde |
| 34. | 5-(2,5-dichlorophenyl)-2-furaldehyde |
| 35. | 2-fluoro-5-nitrobenzaldehyde |
| 36. | 5-(4-nitrophenyl)-2-furaldehyde |
| 37. | 4-dimethylaminobenzaldehyde |
| 38. | 4-[3-(dimethylamino)propoxy]benzaldehyde |
| 39. | 4-n-butylbenzaldehyde |
| 40. | 4-(4-benzylpiperazino)benzaldehyde |
| 41. | 2,2'-bithiophene-5-carboxaldehyde |
| 42. | 4-[4-(1-adamantyl)-1,3-thiazol-2-yl]benzaldehyde |
| 43. | 4-formyl-trans-stilbene |
| 44. | 6-chloroimidazo[2,1-b][1,3]thiazole-5-carbaldehyde |
| 45. | 4-(phenylethynyl)benzaldehyde |
| 46. | 3,3'-(4-formylphenylimino)dipropionitrile |
| 47. | 6-formyl-2-(methylthio)nicotinonitrile |
| 48. | 4-cyanobenzaldehyde |
| 49. | 3-[(4-formylphenoxy)methyl]thiophene-2-carbonitrile |
| 50. | 2-(3-formyl-1h-indol-1-yl)benzonitrile |
| 51. | 2-formyl-6-methoxyphenyl 2,6-difluorobenzoate |
| 52. | tert-butyl 4-formyl-2-methoxyphenyl carbonate |
| 53. | 4-(difluoromethoxy)benzaldehyde |
| 54. | 2-[1-methyl-5-(trifluoromethyl)pyrazol-3-yl]thiophene-5-carboxaldehyde |
| 55. | 5-(3-trifluoromethylphenyl)furan-2-carboxaldehyde |
| 56. | 2,3-difluoro-4-methylbenzaldehyde |
| 57. | 3-chloro-5-(trifluoromethyl)pyridine-2-carboxaldehyde |
| 58. | 4-(trifluoromethoxy)benzaldehyde |
| 59. | 3-[(2,4-difluorophenyl)thio]-5-(trifluoromethyl)pyridine-2-carbaldehyde |
| 60. | 3,5-bis(trifluoromethyl)benzaldehyde |
| 61. | 2,3,5,6-tetrafluorobenzaldehyde |
| 62. | 4-(methylsulfonyl)benzaldehyde |
| 63. | 1-[(4-methylphenyl)sulfonyl]-1h-indole-3-carbaldehyde |
| 64. | 4-formyl-2-methoxyphenyl 2,4,5-trichlorobenzenesulfonate |
| 65. | 4-formylphenyl 2,3,4,5,6-pentamethylbenzenesulfonate |
| 66. | 3-(4-formylphenyl)-2-(pyridin-2-ylsulfonyl)acrylonitrile |
| 67. | 4-acetamidobenzaldehyde |
| 68. | 4-[[5-chloro-2-oxopyrimidin-1(2h)-yl]methoxy]benzaldehyde |
| 69. | 4-(5-formyl-2-furyl)benzene-1-sulfonamide |
| 70. | 3-Benzo[1,3]dioxol-5-yl-2-methyl-propionaldehyde |
| 71. | 3-(phenylthio)butyraldehyde |
| 72. | 3-chloro-4,4,4-trifluoro-2-phenylbutanal |
| 73. | 2-cyano-2-phenylacetaldehyde |
| 74. | 3-methoxyphenylacetaldehyde |
| 75. | pyridine-3-carboxaldehide |
| 76. | 4-chlorobenzaldehyde |
| 77. | 4-cyanobenzaldehyde |

TABLE I-continued

Aldehyde derivatives of formula (V) $R_4$—CO—$R_5$ ($R_5$ = H)

| | |
|---|---|
| 78. | 3-fluorobenzaldehyde |
| 79. | m-tolualdehyde |
| 80. | 2,4-dichlorobenzaldehyde |
| 81. | quinoline-3-carboxaldehyde |
| 82. | 2-(trifluoromethyl)benzaldehyde |
| 83. | methyl 4-formylbenzoate |
| 84. | 4-chloro-3-fluorobenzaldehyde |
| 85. | 4-nitrocinnamaldehyde |
| 86. | 3-thiophenecarboxaldehyde |
| 87. | 3-methoxybenzaldehyde |
| 88. | propionaldehyde |
| 89. | 3,3-dimethylbutyraldehyde |
| 90. | 3-phenylpropionaldehyde |

TABLE II

Acyl chloride derivatives of formula (VIII) R'COZ (Z = Cl)

| | |
|---|---|
| 1. | 3,5-bis(trifluoromethyl)benzoyl chloride |
| 2. | benzoyl chloride |
| 3. | 2-bromobenzoyl chloride |
| 4. | 2-fluorobenzoyl chloride |
| 5. | 2,4-difluorobenzoyl chloride |
| 6. | 2,6-difluorobenzoyl chloride |
| 7. | 2-chlorobenzoyl chloride |
| 8. | 2,4-dichlorobenzoyl chloride |
| 9. | 2-methoxybenzoyl chloride |
| 10. | 2-(trifluoromethyl)benzoyl chloride |
| 11. | o-toluoyl chloride |
| 12. | 3-bromobenzoyl chloride |
| 13. | 3-fluorobenzoyl chloride |
| 14. | 3-chlorobenzoyl chloride |
| 15. | 3,4-dichlorobenzoyl chloride |
| 16. | m-anisoyl chloride |
| 17. | 3,4-dimethoxybenzoyl chloride |
| 18. | 3,4,5-trimethoxybenzoyl chloride |
| 19. | 3,5-dimethoxybenzoyl chloride |
| 20. | 3-(trifluoromethyl)benzoyl chloride |
| 21. | m-toluoyl chloride |
| 22. | 4-bromobenzoyl chloride |
| 23. | 4-fluorobenzoyl chloride |
| 24. | 4-chlorobenzoyl chloride |
| 25. | p-anisoyl chloride |
| 26. | 4-ethoxybenzoyl chloride |
| 27. | 4-n-butoxybenzoyl chloride |
| 28. | 4-biphenylcarbonyl chloride |
| 29. | 4-(trifluoromethyl)benzoyl chloride |
| 30. | 4-tert-butylbenzoyl chloride |
| 31. | p-toluoyl chloride |
| 32. | 4-ethylbenzoyl chloride |
| 33. | 4-n-propylbenzoyl chloride |
| 34. | 4-n-butylbenzoyl chloride |
| 35. | pivaloyl chloride |
| 36. | isobutyryl chloride |
| 37. | 2-ethylhexanoyl chloride |
| 38. | acetyl chloride |
| 39. | phenoxyacetyl chloride |
| 40. | 4-chlorophenoxyacetyl chloride |
| 41. | methoxyacetyl chloride |
| 42. | phenylacetyl chloride |
| 43. | tert-butylacetyl chloride |
| 44. | isovaleryl chloride |
| 45. | propionyl chloride |
| 46. | hydrocinnamoyl chloride |
| 47. | butyryl chloride |
| 48. | pentanoyl chloride |
| 49. | 4-iodobenzoyl chloride |
| 50. | cyclopropanecarbonyl chloride |
| 51. | cyclobutanecarbonyl chloride |
| 52. | cyclopentanecarbonyl chloride |
| 53. | 3-cyclopentylpropionyl chloride |
| 54. | cyclohexanecarbonyl chloride |
| 55. | 4-cyanobenzoyl chloride |
| 56. | 2-furoyl chloride |

TABLE II-continued

Acyl chloride derivatives of formula (VIII) R'COZ (Z = Cl)

| | |
|---|---|
| 57. | 1-naphthoyl chloride |
| 58. | 2-naphthoyl chloride |
| 59. | thiophene-2-carbonyl chloride |
| 60. | thiophene-2-acetyl chloride |
| 61. | (3,4-dimethoxyphenyl) acetyl chloride |
| 62. | 3,5-dichlorobenzoyl chloride |
| 63. | 2,5-difluorobenzoyl chloride |
| 64. | 3,4-difluorobenzoyl chloride |
| 65. | 9-fluorenone-4-carbonyl chloride |
| 66. | 3,5-difluorobenzoyl chloride |
| 67. | benzyloxyacetyl chloride |
| 68. | 3-cyanobenzoyl chloride |
| 69. | (2,5-dimethoxyphenyl)acetyl chloride |
| 70. | 3-methoxyphenylacetyl chloride |
| 71. | nicotinoyl chloride hydrochloride |
| 72. | isonicotinoyl chloride hydrochloride |
| 73. | 2,4,6-trimethylbenzoyl chloride |
| 74. | diphenylacetyl chloride |
| 75. | 2-methylvaleryl chloride |
| 76. | 3,4-methylenedioxybenzoyl chloride |
| 77. | 2,4-dimethoxybenzoyl chloride |
| 78. | 2-phenoxypropionyl chloride |
| 79. | 2-phenylbutyryl chloride |
| 80. | 2-ethylbutyryl chloride |
| 81. | 2,3-dichlorobenzoyl chloride |
| 82. | 4-chlorophenylacetyl chloride |
| 83. | dl-2-methylbutyryl chloride |
| 84. | 2,3-difluorobenzoyl chloride |
| 85. | 1-(4-chlorophenyl)-1-cyclopentanecarbonyl-chloride |
| 86. | 2-ethoxy-1-naphthoyl chloride |
| 87. | benzo[b]thiophene-2-carbonyl chloride |
| 88. | 4-(trifluoromethoxy)benzoyl chloride |
| 89. | 2-(trifluoromethoxy)benzoyl chloride |
| 90. | 3-chlorobenzo[b]thiophene-2-carbonyl chloride |
| 91. | 2-fluoro-3-(trifluoromethyl)benzoyl chloride |
| 92. | 2-fluoro-4-(trifluoromethyl)benzoyl chloride |
| 93. | 2-fluoro-5-(trifluoromethyl)benzoyl chloride |
| 94. | 3-fluoro-5-(trifluoromethyl)benzoyl chloride |
| 95. | 4-fluoro-2-(trifluoromethyl)benzoyl chloride |
| 96. | 4-fluoro-3-(trifluoromethyl)benzoyl chloride |
| 97. | 2-fluoro-6-(trifluoromethyl)benzoyl chloride |
| 98. | 2,3,6-trifluorobenzoyl chloride |
| 99. | 2,4,5-trifluorobenzoyl chloride |
| 100 | 3-(trifluoromethoxy)benzoyl chloride |
| 101 | isoxazole-5-carbonyl chloride |
| 102 | 2,4,6-trifluorobenzoyl chloride |
| 103 | 2,5-bis(trifluoromethyl)benzoyl chloride |
| 104 | 2,3,4-trifluorobenzoyl chloride |
| 105 | 2,4,6-trichlorobenzoyl chloride |
| 106 | 2,4-dichloro-5-fluorobenzoyl chloride |
| 107 | 4-methoxyphenylacetyl chloride |
| 108 | 5-fluoro-2-(trifluoromethyl)benzoyl chloride |
| 109 | 2-chloro-6-fluorobenzoyl chloride |
| 110 | 2-bromo-5-methoxybenzoyl chloride |
| 111 | cyclopentylacetyl chloride |
| 112 | 3-chloro-4-fluorobenzoyl chloride |
| 113 | 3-fluoro-4-(trifluoromethyl)benzoyl chloride |
| 114 | 4-fluorophenylacetyl chloride |
| 115 | 4-tert-butylphenoxyacetyl chloride |
| 116 | 7-Imidazol-1-yl-5,6-dihydro-naphthalene-2-carbonyl chloride |
| 117 | 4-Imidazol-1-ylmethyl-benzoyl chloride |
| 118 | 4-bromo-3-methylbenzoyl chloride |

TABLE III

Isocyanate derivatives of formula (IX) R'NCO

| | |
|---|---|
| 1. | phenyl isocyanate |
| 2. | 2-bromophenyl isocyanate |
| 3. | 2-fluorophenyl isocyanate |
| 4. | 2,4-difluorophenyl isocyanate |
| 5. | 2,6-difluorophenyl isocyanate |

TABLE III-continued

Isocyanate derivatives of formula (IX) R'NCO

| | |
|---|---|
| 6. | 2-chlorophenyl isocyanate |
| 7. | 2,3-dichlorophenyl isocyanate |
| 8. | 2,4-dichlorophenyl isocyanate |
| 9. | 2,5-dichlorophenyl isocyanate |
| 10. | 2,6-dichlorophenyl isocyanate |
| 11. | 2-methoxyphenyl isocyanate |
| 12. | 2,4-dimethoxyphenyl isocyanate |
| 13. | 2,5-dimethoxyphenyl isocyanate |
| 14. | 2-ethoxyphenyl isocyanate |
| 15. | 2-(trifluoromethyl) phenyl isocyanate |
| 16. | o-tolyl isocyanate |
| 17. | 2,6-dimethylphenyl isocyanate |
| 18. | 2-ethylphenyl isocyanate |
| 19. | 3-bromophenyl isocyanate |
| 20. | 3-fluorophenyl isocyanate |
| 21. | 3-chlorophenyl isocyanate |
| 22. | 3,4-dichlorophenyl isocyanate |
| 23. | 3-methoxyphenyl isocyanate |
| 24. | 3-(trifluoromethyl)phenyl isocyanate |
| 25. | m-tolyl isocyanate |
| 26. | 4-bromophenyl isocyanate |
| 27. | 4-fluorophenyl isocyanate |
| 28. | 4-chlorophenyl isocyanate |
| 29. | 4-methoxyphenyl isocyanate |
| 30. | 4-(trifluoromethyl)phenyl isocyanate |
| 31. | p-tolyl isocyanate |
| 32. | benzoyl isocyanate |
| 33. | 1-naphthyl isocyanate |
| 34. | Benzyl isocyanate |
| 35. | 3,5-bis(trifluoromethyl)phenyl isocyanate |
| 36. | 2,5-difluorophenyl isocyanate |
| 37. | 2,4,5-trichlorophenyl isocyanate |
| 38. | 2,4,6-trichlorophenyl isocyanate |
| 39. | 2-isopropylphenyl isocyanate |
| 40. | 2,3-dimethylphenyl isocyanate |
| 41. | 4-methoxy-2-methylphenyl isocyanate |
| 42. | 2,4-dimethylphenyl isocyanate |
| 43. | 2,5-dimethylphenyl isocyanate |
| 44. | 2-ethyl-6-methylphenyl isocyanate |
| 45. | 3-cyanophenyl isocyanate |
| 46. | 5-chloro-2,4-dimethoxyphenyl isocyanate |
| 47. | 3-chloro-4-methylphenyl isocyanate |
| 48. | 3,5-dichlorophenyl isocyanate |
| 49. | 5-chloro-2-methoxyphenyl isocyanate |
| 50. | 3,4,5-trimethoxyphenyl isocyanate |
| 51. | 3,5-dimethoxyphenyl isocyanate |
| 52. | 3-(methylthio)phenyl isocyanate |
| 53. | 3-acetylphenyl isocyanate |
| 54. | 3,4-dimethylphenyl isocyanate |
| 55. | 3,5-dimethylphenyl isocyanate |
| 56. | 2-methoxy-5-methylphenyl isocyanate |
| 57. | 3-ethylphenyl isocyanate |
| 58. | 4-bromo-2-(trifluoromethyl)phenyl isocyanate |
| 59. | 4-chloro-2-(trifluoromethyl)phenyl isocyanate |
| 60. | 4-chloro-3-(trifluoromethyl)phenyl isocyanate |
| 61. | 4-iodophenyl isocyanate |
| 62. | 4-phenoxyphenyl isocyanate |
| 63. | 4-ethoxyphenyl isocyanate |
| 64. | 4-acetylphenyl isocyanate |
| 65. | 4-isopropylphenyl isocyanate |
| 66. | 4-ethylphenyl isocyanate |
| 67. | 4-n-butylphenyl isocyanate |
| 68. | 2,4,6-trimethylphenyl isocyanate |
| 69. | 2-isopropyl-6-methylphenyl isocyanate |
| 70. | 2,6-diethylphenyl isocyanate |
| 71. | 5-chloro-2-methylphenyl isocyanate |
| 72. | 4-chloro-2-methylphenyl isocyanate |
| 73. | 4-(trifluoromethoxy) phenyl isocyanate |
| 74. | 2-chloro-5-(trifluoromethyl) phenyl isocyanate |
| 75. | 2-chloro-6-methylphenyl isocyanate |
| 76. | 2,4,5-trimethylphenyl isocyanate |
| 77. | 3-chloro-2-methoxyphenyl isocyanate |
| 78. | 3-chloro-2-methylphenyl isocyanate |
| 79. | 3-chloro-4-fluorophenyl isocyanate |
| 80. | 4-bromo-2-methylphenyl isocyanate |
| 81. | 4-bromo-2,6-dimethylphenyl isocyanate |
| 82. | 2,6-dibromo-4-fluorophenyl isocyanate |
| 83. | 4-butoxyphenyl isocyanate |
| 84. | 3-fluoro-4-methylphenyl isocyanate |
| 85. | 5-fluoro-2-methylphenyl isocyanate |
| 86. | 2-biphenylyl isocyanate |
| 87. | 4-biphenylyl isocyanate |
| 88. | 2-bromo-4,6-difluorophenyl isocyanate |
| 89. | (r)-(+)-1-phenylethyl isocyanate |
| 90. | 1-(1-naphthyl)ethyl isocyanate |
| 91. | (s)-(+)-1-(1-naphthyl) ethyl isocyanate |
| 92. | 3,4-difluorophenyl isocyanate |
| 93. | 2-(trifluoromethoxy)phenyl isocyanate |
| 94. | 4-benzyloxyphenyl isocyanate |
| 95. | 4-bromo-2-chlorophenyl isocyanate |
| 96. | 4-bromo-2-fluorophenyl isocyanate |
| 97. | 2-fluoro-5-methylphenyl isocyanate |
| 98. | 2,3,4-trifluorophenyl isocyanate |
| 99. | 2-(difluoromethoxy)phenyl isocyanate |
| 100. | 4-(difluoromethoxy)phenyl isocyanate |
| 101. | 2-methylbenzyl isocyanate |
| 102. | 2-chlorobenzyl isocyanate |
| 103. | 4-fluorobenzyl isocyanate |
| 104. | 4-methoxybenzyl isocyanate |
| 105. | 2,6-difluorobenzoyl isocyanate |
| 106. | 4-fluorobenzoyl isocyanate |
| 107. | 2-fluoro-3-(trifluoromethyl)phenyl isocyanate |
| 108. | 2-fluoro-5-(trifluoromethyl)phenyl isocyanate |
| 109. | 2-fluoro-6-(trifluoromethyl)phenyl isocyanate |
| 110. | 4-fluoro-2-(trifluoromethyl)phenyl isocyanate |
| 111. | 2-(tert-butyl)phenyl isocyanate |
| 112. | 3-pyridyl isocyanate |

Accordingly, it is a further object of the present invention a library of two or more amino-phthalazinone derivatives of formula (I)

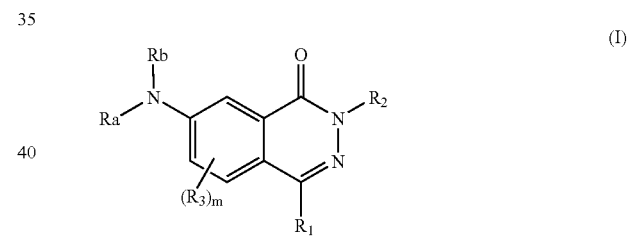

wherein

Ra and Rb are, each independently, a hydrogen atom or a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or one of Ra or Rb is hydrogen or an optionally substituted straight or branched $C_1$-$C_6$ alkyl group, and the other is a group selected from —COR', —CONHR', —COOR' or —SO$_2$R', wherein R' is hydrogen or an optionally substituted group selected from alkyl, cycloalkyl, cycloalkylalkyl, aryl, arylalkyl, heterocyclyl or heterocyclylalkyl, as set forth above;

$R_1$ is a group of formula —CHR$_4$R$_5$ wherein R$_4$ and R$_5$ are, each independently, hydrogen or an optionally substituted group selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_1$ is a group of formula —NHR', —NR'COR", —NR'CONHR" or —NR'SO$_2$R", wherein R' has the above reported meanings other than hydrogen, and R'' is hydrogen or has the meanings set forth above for R';

$R_2$ is a hydrogen atom or it is a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur;

any $R_3$, being placed in one or more of the free positions 5, 6 and 8 of the phthalazinone ring are, independently from each other, halogen, nitro, carboxy, cyano or a group optionally further substituted selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_3$ is a group selected from —COR', —CONHR', —$SO_2$R', —NR'R'', —NR'COR'', —NR'CONHR' or —NR'$SO_2$R'', wherein R' and R'' are, the same or different, hydrogen or a group as set forth above;

m is 0 or an integer from 1 to 3;

or a pharmaceutically acceptable salt thereof.

From all of the above, it is clear to the skilled man that once a library of aminophtalazinone derivatives is thus prepared, for instance consisting of a few thousands of compounds of formula (I), the said library can be very advantageously used for screening towards given target kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumor cells.

In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative protein kinase inhibitors and the potency of selected compounds was determined through a method of assay based on the use of the Multi-Screen-PH 96 well plate (Millipore), in which a phosphocellulose filter paper was placed at each well bottom allowing binding of positive charged substrate after a washing/filtration step.

When a radioactivity labeled phosphate moiety was transferred by the ser/threo kinase to the filter-bound histone, light emitted was measured in a scintillation counter.

Inhibition Assay of cdk2/Cyclin A Activity

Kinase reaction: 1.5 µM histone H1 substrate, 25 µM ATP (0.2 uCi P33γ-ATP), 30 ng of baculovirus co-expressed cdk2/Cyclin A, 10 µM inhibitor in a final volume of 100 µl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca++/Mg++ free and filtered by MultiScreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y = \text{bottom} + (\text{top}-\text{bottom})/(1+10\widehat{\;}((\log IC50 - x)*\text{slope}))$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted $P^{33}$γ-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{Vmax \; \frac{(A)\,(B)}{aKAKB}}{1 + \frac{(A)}{KA} + \frac{(B)}{KB} + \frac{(A)\,(B)}{aKAKB}}$$

where $A = ATP$ and $B$ = histone H1.

In addition the selected compounds have been characterized on a panel of ser/threo kinases strictly related to cell cycle (cdk2/cyclin E, cdk1/cyclin B1, cdk4/Cyclin D1), and also for specificity on MAPK, PKA, EGFR, IGF1-R, Cdc7/dbf4 and aurora-2.

Inhibition Assay of cdk2/Cyclin E Activity

Kinase reaction: 1.5 µM histone H1 (Sigma # H-5505) substrate, 25 µM ATP (0.2 µCi $P^{33}$γ-ATP), 15 ng of baculovirus co-expressed cdk2/GST-Cyclin E, suitable concentrations of inhibitor in a final volume of 100 µl buffer (TRIS HCl 10 mM pH 7.5, $MgCl_2$ 10 mM, 7.5 mM DTT+ 0.2 mg/ml BSA) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay of cdk1/Cyclin B1 Activity

Kinase reaction: 1.5 µM histone H1 (Sigma # H-5505) substrate, 25 µM ATP (0.2 µCi $P^{33}$γ-ATP), 30 ng of baculovirus co-expressed cdkl/Cyclin B1, suitable concentrations of inhibitor in a final volume of 100 µl buffer (TRIS HCl 10 mM pH 7.5, MgCl$_2$ 10 mM, 7.5 mM DTT+ 0.2 mg/ml BSA) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled histone H1 was detected by radioactivity counting in the Top-Count instrument.

Inhibition Assay cdk4/Cyclin D1 Activity

Kinase reaction: 0,4 uM µM mouse GST-Rb(769-921) (# sc-4112 from Santa Cruz) substrate, 10 µM ATP (0.5 µCi P$^{33}$γ-ATP), 100 ng of baculovirus expressed GST-cdk4/GST-Cyclin D1, suitable concentrations of inhibitor in a final volume of 50 µl buffer (TRIS HCl 10 mM pH 7.5, MgCl$_2$ 10 mM, 7.5 mM DTT+ 0.2 mg/ml BSA) were added to each well of a 96 U bottom well plate. After 40 min at 37° C. incubation, reaction was stopped by 20 µl EDTA 120 mM.

Capture: 60 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

Inhibition Assay of MAPK Activity

Kinase reaction: 10 µM MBP (Sigma # M-1891) substrate, 25 µM ATP (0.2 µCi P$^{33}$γ-ATP), 25 ng of bacterially expressed GST-MAPK (Upstate Biotechnology # 14-173), suitable concentrations of inhibitor in a final volume of 100 µl buffer (TRIS HCl 10 mM pH 7.5, MgCl$_2$ 10 mM, 7.5 mM DTT + 0.1 mg/ml BSA) were added to each well of a 96 U bottom well plate. After 15 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled MBP was detected by radioactivity counting in the Top-Count instrument.

Inhibition Assay of PKA Activity

Kinase reaction: 10 µM histone H1 (Sigma # H-5505) substrate, 10 µM ATP (0.2 µCi P$^{33}$γ-ATP), 1 U of bovine heart PKA (Sigma # 2645), suitable concentrations of inhibitor in a final volume of 100 µl buffer (TRIS HCl 10 mM pH 7.5, MgCl$_2$ 10 mM, 7.5 mM DTT+ 0.2 mg/ml BSA) were added to each well of a 96 U bottom well plate. After 5 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled histone H1 was detected by radioactivity counting in the Top-Count instrument.

Inhibition Assay of EGFR Activity

Kinase reaction: 25 nM in house biotinylated PolyGluTyr (Sigma # 0275) substrate, 2.5 µM ATP (0.3 µCi P$^{33}$γ-ATP), 80 ng baculovirus expressed GST-EGFR, suitable concentrations of inhibitor in a final volume of 100 µl buffer (Hepes 50 mM pH 7,5, MnCl$_2$-MgCl$_2$ 3 mM, 1 mM DTT+ 3 µM NaVO3, 0.1 mg/ml BSA) were added to each well of a 96 U bottom well plate. After 5 min. at 37° C. incubation, reaction was stopped by 20 µl EDTA 120 mM.

Capture: 100 µl were transferred from each well to strepta-vidin-Flashplate, to allow biotinylated-substrate binding to plate. Plates were then washed 3 times with 150 µl/well PBS Ca$^{++}$/Mg$^{++}$ free.

Detection: radioactivity counting in the Top-Count instrument.

Inhibition Assay of IGF1-R Activity

The inhibition assay of IGF1-R activity was performed according to the following protocol.

Kinase reaction: 10 µM biotinylated MBP (Sigma cat. # M-1891) substrate, 0-20 µM inhibitor, 6 µM cold ATP, 2 nM $^{33}$P-ATP, and 22.5 ng IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 15 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Results: Experimental data were analyzed with the program GraphPad Prizm.

In addition, the inhibiting activity of putative protein kinase inhibitors and the potency of selected compounds was also determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labeled phosphate moiety was transferred by the ser/threo kinase to the biotinylated histone peptide, light emitted was measured in a scintillation counter.

Inhibition Assay of cdk5/p25 Activity

The inhibition assay of cdk5/p25 activity was performed according to the following protocol.

Kinase reaction: 1.0 µM biotinylated histone peptide substrate, 0.25 uCi P33g-ATP, 4 nM cdk5/p25 complex, 0-100 µM inhibitor in a final volume of 100 µl buffer (Hepes 20 mM pH 7.5, MgCl2 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100X(1-(\text{Unknown}-\text{Bkgd})/(\text{Enz. Control}-\text{Bkgd}))$$

IC50 values were calculated using a variation of the four parameter logistics equation:

$$Y=100/[1+10\textasciicircum((\text{Log EC50}-X)*\text{Slope})]$$

Where X=log(uM) and Y=% Inhibition.

Inhibition Assay of Cdc7/dbf4 Activity

The inhibition assay of Cdc7/dbf4 activity was performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:
  10 μl substrate (biotinylated MCM2, 6 μM final concentration)
  10 μl enzyme (Cdc7/Dbf4, 12.5 nM final concentration)
  10 μl test compound (12 increasing concentrations in the nM to μM range to generate a dose-response curve)
  10 μl of a mixture of cold ATP (10 μM final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 20 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilter® GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

Inhibition Assay of Aurora-2 Activity

The inhibiting activity and the potency of selected compounds was determined through a method of assay based on the use of the streptavidin scintillation proximity assay beads (amershampharmacia biotech) run in a 96 well plates. At the end of the reaction, the biotinylated peptide substrate was captured with the beads and subsequently allowed to stratify using $CsCl_2$.

When a radioactivity labeled phosphate moiety was transferred by the kinase to the beads-bound peptide, light emitted was measured in a scintillation counter.

The inhibition assay of Aurora-2 activity was performed in 96 wells plate according to the following protocol.

Kinase reaction: 8 μM biotinylated peptide (4 repeats of LRRWSLG), 10 μM ATP (0.5 uCi $P^{33}$g-ATP), 10 nM Aurora2, 10 μM inhibitor in a final volume of 60 μl buffer (HEPES 50 mM pH 7.0, $MgCl_2$ 10 mM, 1 mM DTT, 0.125 mg/ml BSA, 3 μM orthovanadate) were added to each well of a 96 U bottom well plate. After 30 minutes at room temperature incubation, reaction was stopped and biotinylated peptide captured by adding 100 μl of bead suspension.

Stratification: 100 μl of CsCl2 7.5 M were added to each well and let stand one hour before radioactivity was counted in the Top-Count instrument.

Results: data were analyzed and expressed as % inhibition referred to total activity of enzyme (=100%).

All compounds showing inhibition ≧60% were further analyzed in order to study the potency of the inhibitor through IC50 calculation.

The protocol used was the same described above, except that serial dilution of the inhibitor was used. Experimental data were fitted by nonlinear regression using the following equation:

$$v = v_0 + \frac{(v_0 - v_b)}{1 + 10^{n(\log IC_{50} - \log[I])}}$$

With $v_b$ as the baseline velocity, v as the observed reaction velocity, $v_o$ as the velocity in the absence of inhibitors, and [I] as the inhibitor concentration.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, exemestane, formestane, anastrozole, letrozole, fadrozole, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, tamoxifen, raloxifen, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerin and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples illustrate but do not limit the present invention.

General Methods

Flash chromatografy was performed on silica gel (Merck grade 9385, 60 Å). HPLC/MS was performed on a Waters X Terra RP 18 (4.6×50 mm, 3.5 μm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 min. UV detection at 220 nm and 254 nm. Flow rate 1 ml/min. Injection volume 10 μl. Full scan, mass range from 100 to 800 amu. Capillary voltage was 2.5 KV; Source temp. was 120° C.; Cone was 10 V. Retention Times (HPLC r.t.) are given in minutes at 220 nm or 254 nm. Mass are given as m/z ratio.

When necessary compounds have been purified by Preparative HPLC on a Waters Symmetry C18 (19×50 mm, 5 um) column using a Waters preparative HPLC 600 equipped with a 996 Waters PDA detector and a Micromass mod. ZMD single quadrupole mass spectrometer, electrospray ionisation, positive mode. Mobile phase A was water 0.01% TFA, and Mobile phase B was acetonitrile. Gradient from 10 to 90% B in 8 min, hold 90% B 2 min. Flow rate 20 ml/m.

$^1$H-NMR spectroscopy was performed on a Mercury VX 400 operating at 400.45 MHz equipped with a 5 mm double resonance probe (1H {15N-31P} ID_PFG Varian).

EXAMPLE 1

6-nitro-3-bromo-3H-isobenzofuran-1-one (II)

To 125 ml of a dichloromethane solution of 6-nitrophtalide (8.0 g, 0.047 mol), bromine (8.25 g, 0.052 mol, 1.15 eq) and hydrogen peroxide (5.07 g of a 35% solution in water, equivalent to 1.77 of hydrogen peroxide, 0.052 mol, 1.15 eq) were added. The mixture was gently refluxed for 11 hours, then cooled down and concentrated by solvent evaporation. The aqueous layer was separated, and the organic phase washed with water before drying up ($Na_2SO_4$).

After evaporation of the solvent the crude residue was purified by flash chromatography over silica gel (hexane-ethyl acetate 8-2 to 7-3). 8.18 g of the titled compound were obtained. $[M-1]^-=257$; HPLC r.t. 5.37; $^1$H-NMR ($CDCl_3$), diagnostic signals (ppm): 7.47 (s, 1H), 7.86 (d, 1H), 8.67 (dd, 1H), 8.74 (d, 1H).

EXAMPLE 2

(5-Amino-3-oxo-1,3-dihydro-isobenzofuran-1-yl)-triphenyl-phosphonium bromide (III)

A solution of 6-nitro-3-bromo-3H-isobenzofuran-1-one (8.7 g, 0.034 mol) in ethyl propionate (464 ml) was heated to 70-75° C., and stirred while 313 ml of an ethyl propionate solution of triphenyl phosphine (36 g, 0.137 mol, 4 eq) were added dropwise over a time of 7 hours. Heating and stirring were continued overnight, and then the mixture was cooled down to room temperature. The precipitate was collected, dried up under vacuum and purified by flash chromatography over silica gel. A gradient of dichloromethane-methanol-acetic acid, from 97-3-0 to 93-5-2 was used as the eluant, to yield 6.2 g of the title compound. $[M]^+=410$; HPLC r.t. 4.72; $^1$H-NMR (DMSO-$d_6$), diagnostic signals (ppm): 6.01 (br. s, 2H exchangeable with deuterated water), 6.49 (dd, 1H), 6.80 (d, 1H), 6.87 (d, 1H), 7.62-8.00 (m, 15H), 8.17 (s, 1H).

EXAMPLE 3

(5-{2-Methoxy-4-[3-(4-resin-benzylcarbamoyl)-propoxy]-benzylamino}-3-oxo-1,3-dihydro-isobenzofuran-1-yl)-triphenyl-phosphonium bromide The compound of example 2 (252 mg, 0.514 mmol) was dissolved in 15.25 ml of a solvent mixture made up of dichloromethane (13.5 ml), trifluoroethanol (1.5 ml) and acetic acid (0.25 ml). *Novabiochem* 4-(4-Formyl-3-methoxyphenoxy) butyryl aminomethylated resin (326 mg, declared substitution 0.94 mmol/g, 0.6 eq.) was poured into the solution, and the resulting suspension was gently stirred for 9 hours before adding dropwise the pyridine-borane complex (250 μl, ~6 mmol, 10 eq.). After 40 hours the resin was filtered, washed with dichloromethane, methanol and again dichloromethane, hence dried under vacuum (518 mg, calculated loading: 0.78 mmol/g; IR: 1787 $cm^{-1}$, lactone stretching band).

EXAMPLE 4

4-[3-Methoxy-4-({3-oxo-1-[1-pyridin-3-yl-methylidene]-1,3-dihydro-isobenzofuran-5-ylamino}-methyl)-phenoxy]-N-(4-resin-benzyl)-butyramide (5-{2-Methoxy-4-[3-(4-resin-benzylcarbamoyl)-propoxy]-benzylamino}-3-oxo-1,3-dihydro-isobenzofuran-1-yl)-triphenyl-phosphonium bromide of example 3 (100 mg, 0.078 meq) was suspended in dried dichloromethane (3 ml); pyridine-3-carboxaldehyde (50 µl, about ~6 eq.) was added, followed by TEA (50 µl). Stirring at room temperature was maintained for 20 hours then the resin was filtered and washed with dichloromethane, methanol, and again dichloromethane before drying under vacuum (IR: 1776 cm$^{-1}$).

EXAMPLE 5

N-{2-Methoxy-4-[3-(4-resin-benzylcarbamoyl)-propoxy]-benzyl}-N-{3-oxo-1-[1-pyridin-3-yl-methylidene]-1,3-dihydro-isobenzofuran-5-yl}-benzamide 4-[3-Methoxy-4-({3-oxo-1-[1-pyridin-3-yl-methylidene]-1,3-dihydro-isobenzofuran-5-ylamino}-methyl)-phenoxy]-N-(4-resin-benzyl)-butyramide of example 4 was suspended in dried dichloromethane (3 ml); diisopropyl ethylamine (200 µl) and benzoyl chloride (100 µl, ~10 eq.) were added in this order. After stirring at room temperature for 20 hours, the resin was filtered and washed with dichloromethane, methanol, and again dichloromethane before drying under vacuum (IR: 1786 cm$^{-1}$).

EXAMPLE 6

4-[3-Methoxy-4-(1-{3-oxo-1-[1-pyridin-3-yl-methylidene]-1,3-dihydro-isobenzofuran-5-yl}-3-p-tolyl-ureidomethyl)-phenoxy]-N-(4-resin-benzyl)-butyramide 4-[3-Methoxy-4-({3-oxo-1-[1-pyridin-3-yl-methylidene]-1,3-dihydro-isobenzofuran-5-ylamino}-methyl)-phenoxy]-N-(4-resin-benzyl)-butyramide of example 4 was suspended in dried dichloromethane (3 ml) and p-toluyl isocyanate (100 µl, ~10 eq.) was added. After stirring at room temperature for 20 hours, the resin was filtered and washed with dichloromethane, methanol, and again dichloromethane before drying under vacuum.

EXAMPLE 7

N-{2-Methoxy-4-[3-(4-resin-benzylcarbamoyl)-propoxy]-benzyl}-N-(4-oxo-1-pyridin-3-ylmethyl-3,4-dihydro-phthalazin-6-yl)-benzamide N-{2-Methoxy-4-[3-(4-resin-benzylcarbamoyl)-propoxy]-benzyl}-N-{3-oxo-1-[1-pyridin-3-yl-methylidene]-1,3-dihydro-isobenzofuran-5-yl}-benzamide of example 5 was suspended in dimethylformammide (3 ml) and aqueous hydrazine (approximately 25% solution) was added (400 µl, about 40 eq.). After stirring at room temperature for 20 hours, the resin was filtered, washed with dimethylformammide, methanol and dichloromethane before drying under vacuum. (IR: disappearance of lactone stretching band).

Example 8

4-{3-Methoxy-4-[1-(4-oxo-1-pyridin-3-ylmethyl-3,4-dihydro-phthalazin-6-yl)-3-p-tolyl-ureidomethyl]-phenoxy}-N-(4-resin-benzyl)-butyramide 4-[3-Methoxy-4-(1-{3-oxo-1-[1-pyridin-3-yl-methylidene]-1,3-dihydro-isobenzofuran-5-yl}-3-p-tolyl-ureidomethyl)-phenoxy]-N-(4-resin-benzyl)-butyramide of example 6 was suspended in dimethylformammide (3 ml) and aqueous hydrazine (approximately 25% solution) was added (400 µl, about 40 eq.). After stirring at room temperature for 20 hours, the resin was filtered, washed with dimethylformammide, methanol and dichloromethane before drying under vacuum.

EXAMPLE 9

N-(4-Oxo-1-pyridin-3-ylmethyl-3,4-dihydro-phthalazin-6-yl)-benzamide

N-{2-Methoxy-4-[3-(4-resin-benzylcarbamoyl)-propoxy]-benzyl}-N-(4-oxo-1-pyridin-3-ylmethyl-3,4-dihydro-phthalazin-6-yl)-benzamide of example 7 was suspended in a solution of 20% TFA in DCM (3 ml), and stirred at room temperature for 2 hours. The resin was filtered and the solution collected and dried up yielding 15 mg of title compound. [M+1]$^+$=357; HPLC r.t. 4.02; $^1$H-NMR (DMSO-d6), diagnostic signals (ppm): 4.39 (s, 2H), 7.47-7.62 (m, 3H), 7.93-8.05 (m, 3H), 8.26 (dd, 1H), 8.54 (m, 1H), 8.65 (br. S, 1H), 8.76 (d, 1H), 10.73 (s, 1H, exchangeable with water), 12.45 (s, 1H, exchangeable with water).

EXAMPLE 10

1-(4-Oxo-1-pyridin-3-ylmethyl-3,4-dihydro-phthalazin-6-yl)-3-p-tolyl-urea

4-{3-Methoxy-4-[1-(4-oxo-1-pyridin-3-ylmethyl-3,4-dihydro-phthalazin-6-yl)-3-p-tolyl-ureidomethyl]-phenoxy}-N-(4-methyl-benzyl)-butyramide of example 8 was suspended in a solution of 20% TFA in DCM (3 ml), and stirred at room temperature for 2 hours. The resin was filtered and the solution collected and dried up yielding 11 mg of title compound. [M+1]$^+$=386; HPLC r.t. 4.72; $^1$H-NMR (DMSO-d6), diagnostic signals (ppm): 2.23 (s, 3H), 4.26 (s, 2H), 7.10 (d, 2H), 7.29 (m, 1H) 7.33 (d, 2H), 7.64 (m, 1H), 7.83 (dd, 1H), 7.89 (d, 1H), 8.40 (m, 2H), 8.56 (d, 1H), 8.70 (br. S, 1H), 9.22 (br. s, 1H), 12.38 (br. s, 1H).

By working in an analogous way and by reacting the compound of formula (III) with the appropriate aldehyde of formula (V) and then with the proper acyl chloride derivative of formula (VIII) or isocyante of formula (IX), the following compounds were prepared:

7-Amino-4-(4-chloro-benzyl)-2H-phthalazin-1-one [M+1]$^+$=286; HPLC r.t. 4.62; $^1$H-NMR (DMSO-d6), diagnostic signals (ppm): 4.11 (s, 2H), 6.97 (dd, 1H), 7.24-7.32 (m, 5H), 7.56 (d, 1H), 12.05 (s, 1H, exchangeable with deuterated water).

7-Amino-4-(4-methoxy-benzyl)-2H-phthalazin-1-one [M+1]$^+$=282; HPLC r.t. 3.83; $^1$H-NMR (DMSO-d6), diagnostic signals (ppm): 3.68 (s, 3H) 4.04 (s, 2H), 6.10 (s, 2H, exchangeable with deuterated water), 6.82 (d, 2H), 6.97 (dd, 1H), 7.17 (d, 2H), 7.23 (d, 1H), 7.57 (d, 1H).

7-Amino-4-(4-nitro-benzyl)-2H-phthalazin-1-one [M+1]$^+$=297; $^1$H-NMR (DMSO-d6), diagnostic signals (ppm): 4.29 (s, 2H), 6.18 (s, 2H, exchangeable with deuterated water), 7.00 (dd, 1H), 7.26 (d, 1H), 7.57 (m, 3H), 8.14 (d, 2H).

N-(4-Oxo-1-pyridin-3-ylmethyl-3,4-dihydro-phthalazin-6-yl)-propionamide; [M+H]+=309; HPLC r.t. 2.88.

N-(4-Oxo-1-pyridin-3-ylmethyl-3,4-dihydro-phthalazin-6-yl)-4-trifluoromethyl-benzamide; [M+H]+=425; HPLC r.t. 5.1.

Furan-2-carboxylic acid (4-oxo-1-pyridin-3-ylmethyl-3,4-dihydro-phthalazin-6-yl)-amide; [M+H]+=346; HPLC r.t. 3.37.

N-(4-Oxo-1-pyridin-3-ylmethyl-3,4-dihydro-phthalazin-6-yl)-3-cyclopentyl-propionamide; [M+H]+=377; HPLC r.t. 4.99.

2-Propyl-pentanoic acid (4-oxo-1-pyridin-3-ylmethyl-3,4-dihydro-phthalazin-6-yl)-amide; [M+H]+=379; HPLC r.t. 5.09.

1-(4-Oxo-1-pyridin-3-ylmethyl-3,4-dihydro-phthalazin-6-yl)-3-(3-trifluoromethyl-phenyl)-urea; [M+H]+=440; HPLC r.t. 5.29.

1-(3-Methoxy-phenyl)-3-(4-oxo-1-pyridin-3-ylmethyl-3,4-dihydro-phthalazin-6-yl)-urea; [M+H]+=402; HPLC r.t. 4.33.

1-(4-Oxo-1-pyridin-3-ylmethyl-3,4-dihydro-phthalazin-6-yl)-3-p-tolyl-urea; [M+H]+=386; HPLC r.t. 4.62.

1-(2,4-Difluoro-phenyl)-3-(4-oxo-1-pyridin-3-ylmethyl-3,4-dihydro-phthalazin-6-yl)-urea; [M+H]+=408; HPLC r.t. 4.58.

1-(3,4-Dichloro-phenyl)-3-(4-oxo-1-pyridin-3-ylmethyl-3,4-dihydro-phthalazin-6-yl)-urea; [M+H]+=440; HPLC r.t. 5.59.

N-[1-(4-Chloro-benzyl)-4-oxo-3,4-dihydro-phthalazin-6-yl]-propionamide; [M+H]+=342; HPLC r.t. 5.18.

N-[1-(4-Chloro-benzyl)-4-oxo-3,4-dihydro-phthalazin-6-yl]-4-trifluoromethyl-benzamide; [M+H]+=458; HPLC r.t. 7.13.

Furan-2-carboxylic acid [1-(4-chloro-benzyl)-4-oxo-3,4-dihydro-phthalazin-6-yl]-amide; [M+H]+=380; HPLC r.t. 5.66.

N-[1-(4-Chloro-benzyl)-4-oxo-3,4-dihydro-phthalazin-6-yl]-3-cyclopentyl-propionamide; [M+H]+=410; HPLC r.t. 7.22.

2-Propyl-pentanoic acid [1-(4-chloro-benzyl)-4-oxo-3,4-dihydro-phthalazin-6-yl]-amide; [M+H]+=412; HPLC r.t. 7.33.

1-[1-(4-Chloro-benzyl)-4-oxo-3,4-dihydro-phthalazin-6-yl]-3-(3-trifluoromethyl-phenyl)-urea; [M+H]+=473; HPLC r.t. 7.26.

1-[1-(4-Chloro-benzyl)-4-oxo-3,4-dihydro-phthalazin-6-yl]-3-(3-methoxy-phenyl)-urea; [M+H]+=435; HPLC r.t. 6.43.

1-[1-(4-Chloro-benzyl)-4-oxo-3,4-dihydro-phthalazin-6-yl]-3-p-tolyl-urea; [M+H]+=419; HPLC r.t. 6.74.

1-[1-(4-Chloro-benzyl)-4-oxo-3,4-dihydro-phthalazin-6-yl]-3-(2,4-difluoro-phenyl)-urea; [M+H]+=441; HPLC r.t. 6.71.

N-[1-(4-Cyano-benzyl)-4-oxo-3,4-dihydro-phthalazin-6-yl]-propionamide; [M+H]+=333; HPLC r.t. 4.26.

N-[1-(4-Cyano-benzyl)-4-oxo-3,4-dihydro-phthalazin-6-yl]-4-trifluoromethyl-benzamide; [M+H]+=449; HPLC r.t. 6.3.

Furan-2-carboxylic acid [1-(4-cyano-benzyl)-4-oxo-3,4-dihydro-phthalazin-6-yl]-amide; [M+H]+=371; HPLC r.t. 4.72.

N-[1-(4-Cyano-benzyl)-4-oxo-3,4-dihydro-phthalazin-6-yl]-3-cyclopentyl-propionamide; [M+H]+=401; HPLC r.t. 6.3.

2-Propyl-pentanoic acid [1-(4-cyano-benzyl)-4-oxo-3,4-dihydro-phthalazin-6-yl]-amide; [M+H]+=403; HPLC r.t. 6.42.

1-[1-(4-Cyano-benzyl)-4-oxo-3,4-dihydro-phthalazin-6-yl]-3-(3-trifluoromethyl-phenyl)-urea; [M+H]+=464; HPLC r.t. 6.46; $^1$H-NMR (DMSO-d6), diagnostic signals (ppm): 4.34 (s, 2H), 7.34 (d, 1H), 7.47-7.55 (m, 3H), 7.59 (d, 1H), 7.73 (d, 2H), 7.80-7.88 (m, 2H), 8.00 (s, 1H), 8.43 (d, 1H), 9.20 (s, 1H), 9.40 (s, 1H), 12.44 (br. s, 1H).

1-[1-(4-Cyano-benzyl)-4-oxo-3,4-dihydro-phthalazin-6-yl]-3-(3-methoxy-phenyl)-urea; [M+H]+=426; HPLC r.t. 5.59.

1-[1-(4-Cyano-benzyl)-4-oxo-3,4-dihydro-phthalazin-6-yl]-3-p-tolyl-urea; [M+H]+=410; HPLC r.t. 5.89.

1-[1-(4-Cyano-benzyl)-4-oxo-3,4-dihydro-phthalazin-6-yl]-3-(2,4-difluoro-phenyl)-urea; [M+H]+=432; HPLC r.t. 6.

N-[1-(3-Fluoro-benzyl)-4-oxo-3,4-dihydro-phthalazin-6-yl]-propionamide; [M+H]+=326; HPLC r.t. 4.69; $^1$H-NMR (DMSO-d6), diagnostic signals (ppm): 1.08 (t, 3H), 2.35 (q, 2H), 4.24 (s, 2H), 7.00 (m, 1H), 7.11 (m, 2H), 7.29 (m, 1H), 7.90 (d, 1H), 7.95 (dd, 1H), 8.53 (d, 1H), 10.35 (br. s, 1H), 12.42 (br. S, 1H).

N-[1-(3-Fluoro-benzyl)-4-oxo-3,4-dihydro-phthalazin-6-yl]-4-trifluoromethyl-benzamide; [M+H]+=442; HPLC r.t. 6.68.

Furan-2-carboxylic acid [1-(3-fluoro-benzyl)-4-oxo-3,4-dihydro-phthalazin-6-yl]-amide; [M+H]+=364; HPLC r.t. 5.16.

N-[1-(3-Fluoro-benzyl)-4-oxo-3,4-dihydro-phthalazin-6-yl]-3-cyclopentyl-propionamide; [M+H]+=394; HPLC r.t. 6.73.

2-Propyl-pentanoic acid [1-(3-fluoro-benzyl)-4-oxo-3,4-dihydro-phthalazin-6-yl]-amide; [M+H]+=396; HPLC r.t. 6.85.

1-[1-(3-Fluoro-benzyl)-4-oxo-3,4-dihydro-phthalazin-6-yl]-3-(3-trifluoromethyl-phenyl)-urea; [M+H]+=457; HPLC r.t. 6.86.

1-[1-(3-Fluoro-benzyl)-4-oxo-3,4-dihydro-phthalazin-6-yl]-3-(3-methoxy-phenyl)-urea; [M+H]+=419; HPLC r.t. 5.98.

N-[1-(3-Methyl-benzyl)-4-oxo-3,4-dihydro-phthalazin-6-yl]-propionamide; [M+H]+=322; HPLC r.t. 4.92.

N-[1-(3-Methyl-benzyl)-4-oxo-3,4-dihydro-phthalazin-6-yl]-4-trifluoromethyl-benzamide; [M+H]+=438; HPLC r.t. 6.93.

Furan-2-carboxylic acid [1-(3-methyl-benzyl)-4-oxo-3,4-dihydro-phthalazin-6-yl]-amide; [M+H]+=360; HPLC r.t. 5.38.

N-[1-(3-Methyl-benzyl)-4-oxo-3,4-dihydro-phthalazin-6-yl]-3-cyclopentyl-propionamide; [M+H]+=390; HPLC r.t. 6.95.

2-Propyl-pentanoic acid [1-(3-methyl-benzyl)-4-oxo-3,4-dihydro-phthalazin-6-yl]-amide; [M+H]+=392; HPLC r.t. 7.08.

1-[1-(3-Methyl-benzyl)-4-oxo-3,4-dihydro-phthalazin-6-yl]-3-(3-trifluoromethyl-phenyl)-urea; [M+H]+=453; HPLC r.t. 7.04.

1-[1-(3-Methyl-benzyl)-4-oxo-3,4-dihydro-phthalazin-6-yl]-3-(3-methoxy-phenyl)-urea; [M+H]+=415; HPLC r.t. 6.18.

1-[1-(3-Methyl-benzyl)-4-oxo-3,4-dihydro-phthalazin-6-yl]-3-p-tolyl-urea; [M+H]+=399; HPLC r.t. 6.48.

1-[1-(3-Methyl-benzyl)-4-oxo-3,4-dihydro-phthalazin-6-yl]-3-(2,4-difluoro-phenyl)-urea; [M+H]+=421; HPLC r.t. 6.5.

N-[1-(2,4-Dichloro-benzyl)-4-oxo-3,4-dihydro-phthalazin-6-yl]-propionamide; [M+H]+=376; HPLC r.t. 5.83;

¹H-NMR (DMSO-d6), diagnostic signals (ppm): 1.09 (t, 3H), 2.37 (q, 2H), 4.33 (s, 2H), 7.30 (d, 1H), 7.32 (dd, 1H), 7.60 (d, 1H), 7.93 (d, 1H), 8.02 (dd, 1H), 8.56 (d, 1H), 10.39 (s, 1H), 12.33 (s, 1H).

N-[1-(2,4-Dichloro-benzyl)-4-oxo-3,4-dihydro-phthalazin-6-yl]-4-trifluoromethyl-benzamide; [M+H]+=492; HPLC r.t. 7.68; ¹H-NMR (DMSO-d6), diagnostic signals (ppm): 4.37 (s, 2H), 7.30-7.37 (m, 2H), 7.62 (d, 1H), 7.94 (d, 2H), 8.02 (d, 1H), 8.19 (d, 2H), 8.27 (dd, 1H), 8.77 (d, 1H), 10.96 (br. S, 1H), 12.41 (br. S, 1H).

Furan-2-carboxylic acid [1-(2,4-dichloro-benzyl)-4-oxo-3,4-dihydro-phthalazin-6-yl]-amide; [M+H]+=414; HPLC r.t. 6.26.

N-[1-(2,4-Dichloro-benzyl)-4-oxo-3,4-dihydro-phthalazin-6-yl]-succinamic acid ethyl ester; [M+H]+=; HPLC r.t. 6.11.

N-[1-(2,4-Dichloro-benzyl)-4-oxo-3,4-dihydro-phthalazin-6-yl]-3-cyclopentyl-propionamide; [M+H]+=444; HPLC r.t. 7.82; ¹H-NMR (DMSO-d6), diagnostic signals (ppm): 1.00-1.85 (m, 11H), 2.37 (t, 2H), 4.33 (s, 2H), 7.30 (d, 1H), 7.32 (dd, 1H), 7.60 (dd, 1H), 7.92 (d, 1H), 8.00 (dd, 1H), 8.56 (dd, 1H), 10.40 (br. S., 1H), 12.33 (br. S., 1H).

2-Propyl-pentanoic acid [1-(2,4-dichloro-benzyl)-4-oxo-3,4-dihydro-phthalazin-6-yl]-amide; [M+H]+=446; HPLC r.t. 7.94; ¹H-NMR (DMSO-d6), diagnostic signals (ppm): 1.00-1.85 (m, 9H), 1.58-1.66 (m, 2H), 2.37 (m, 2H), 4.33 (s, 2H), 7.30 (d, 1H), 7.32 (dd, 1H), 7.60 (d, 1H), 7.92 (d, 1H), 8.00 (dd, 1H), 8.56 (dd, 1H), 10.40 (br. S, 1H), 12.33 (br. S, 1H).

1-[1-(2,4-Dichloro-benzyl)-4-oxo-3,4-dihydro-phthalazin-6-yl]-3-(3-trifluoromethyl-phenyl)-urea; [M+H]+=507; HPLC r.t. 7.83.

1-[1-(2,4-Dichloro-benzyl)-4-oxo-3,4-dihydro-phthalazin-6-yl]-3-(3-methoxy-phenyl)-urea; [M+H]+=469; HPLC r.t. 7.02; ¹H-NMR (DMSO-d6), diagnostic signals (ppm): 3.73 (s, 3H), 4.33 (s, 2H), 6.58 (m, 1H), 6.96 (m, 1H), 7.15-7.22 (m, 2H), 7.28-7.36 (m, 2H), 7.61 (d, 1H), 7.82-7.90 (m, 2H), 8.44 (d, 1H), 8.91 (br. S, 1H), 9.35 (br. S, 1H), 12.31 (br.s, 1H).

1-[1-(2,4-Dichloro-benzyl)-4-oxo-3,4-dihydro-phthalazin-6-yl]-3-p-tolyl-urea; [M+H]+=453; HPLC r.t. 7.35.

1-[1-(2,4-Dichloro-benzyl)-4-oxo-3,4-dihydro-phthalazin-6-yl]-3-(2,4-difluoro-phenyl)-urea; [M+H]+=475; HPLC r.t. 7.38; ¹H-NMR (DMSO-d6), diagnostic signals (ppm): 4.33 (s, 2H), 7.06 (m, 1H), 7.25-7.36 (m, 3H), 7.61 (d, 1H), 7.85 (dd, 1H), 7.88 (d, 1H), 8.03 (m, 1H), 8.45 (d, 1H), 8.75 (s, 1H), 9.71 (s, 1H), 12.33 (s, 1H).

N-(4-Oxo-1-quinolin-3-ylmethyl-3,4-dihydro-phthalazin-6-yl)-propionamide; [M+H]+=359; HPLC r.t. 4.01.

N-(4-Oxo-1-quinolin-3-ylmethyl-3,4-dihydro-phthalazin-6-yl)-4-trifluoromethyl-benzamide; [M+H]+=475; HPLC r.t. 6; ¹H-NMR (DMSO-d6), diagnostic signals (ppm): 4.51 (s, 2H), 7.57 (dt, 1H), 7.69 (dt, 1H) 7.87-8.00 (m, 4H), 8.09 (d, 1H), 8.15-8.20 (m, 3H), 8.23 (dd, 1H), 8.76 (d, 1H), 8.92 (d, 1H), 10.92 (s, 1H), 12.49 (s, 1H).

N-(4-Oxo-1-quinolin-3-ylmethyl-3,4-dihydro-phthalazin-6-yl)-succinamic acid ethyl ester; [M+H]+=431; HPLC r.t. 4.37.

N-(4-Oxo-1-quinolin-3-ylmethyl-3,4-dihydro-phthalazin-6-yl)-3-cyclopentyl-propionamide; [M+H]+=427; HPLC r.t. 5.97.

2-Propyl-pentanoic acid (4-oxo-1-quinolin-3-ylmethyl-3,4-dihydro-phthalazin-6-yl)-amide; [M+H]+=429; HPLC r.t. 6.08. ¹H-NMR (DMSO-d6), diagnostic signals (ppm): 0.80-0.88 (m, 6H), 1.18-1.29 (m, 4H), 1.29-1.64 (m, 4H), 2.37-2.48 (m, 1H), 4.48 (s, 2H), 7.55 (m, 1H), 7.70 (m, 1H), 7.88 (dd, 1H), 7.95-8.01 (m, 3H), 8.17 (d, 1H), 8.58 (d, 1H), 8.91 (d, 1H), 10.36 (br. s, 1H), 12.42 (br. S, 1H).

1-(4-Oxo-1-quinolin-3-ylmethyl-3,4-dihydro-phthalazin-6-yl)-3-(3-trifluoromethyl-phenyl)-urea; [M+H]+=490; HPLC r.t. 6.16.

1-(4-Oxo-1-quinolin-3-ylmethyl-3,4-dihydro-phthalazin-6-yl)-3-(3-methoxy-phenyl)-urea; [M+H]+=452; HPLC r.t. 5.27; ¹H-NMR (DMSO-d6), diagnostic signals (ppm): 3.72 (s, 3H), 4.47 (s, 2H), 6.57 (m, 1H), 6.94 (m, 1H), 7.19 (m, 2H), 7.55 (dd, 1H), 7.69 (dd, 1H), 7.81 (dd, 1H), 7.88 (dd, 1H), 7.96 (m, 2H), 8.16 (d, 1H), 8.44 (d, 1H), 8.82 (br. s, 1H), 8.91 (d, 1H), 9.25 (br. s, 1H), 12.40 (br. s, 1H).

1-(4-Oxo-1-quinolin-3-ylmethyl-3,4-dihydro-phthalazin-6-yl)-3-p-tolyl-urea; [M+H]+=436; HPLC r.t. 5.56.

1-(4-Oxo-1-quinolin-3-ylmethyl-3,4-dihydro-phthalazin-6-yl)-3-(2,4-difluoro-phenyl)-urea; [M+H]+=458; HPLC r.t. 5.55; ¹H-NMR (DMSO-d6), diagnostic signals (ppm): 4.48 (s, 2H), 7.05 (m, 1H), 7.30 (m, 1H), 7.54 (dt, 1H), 7.69 (dt, 1H), 7.79 (dd, 1H), 7.87 (d, 1H), 7.95-8.07 (m, 2H), 8.16 (d, 1H), 8.44 (d, 1H), 8.61 (d, 1H), 8.90 (s, 1H), 9.56 (s, 1H) 12.41 (s, 1H).

1-(4-Oxo-1-quinolin-3-ylmethyl-3,4-dihydro-phthalazin-6-yl)-3-(3,4-dichloro-phenyl)-urea; [M+H]+=491; HPLC r.t. 6.51.

N-[4-Oxo-1-(2-trifluoromethyl-benzyl)-3,4-dihydro-phthalazin-6-yl]-propionamide; [M+H]+=376; HPLC r.t. 5.41.

N-[4-Oxo-1-(2-trifluoromethyl-benzyl)-3,4-dihydro-phthalazin-6-yl]-4-trifluoromethyl-benzamide; [M+H]+=492; HPLC r.t. 7.23.

Furan-2-carboxylic acid [4-oxo-1-(2-trifluoromethyl-benzyl)-3,4-dihydro-phthalazin-6-yl]-amide; [M+H]+=414; HPLC r.t. 5.82.

N-[4-Oxo-1-(2-trifluoromethyl-benzyl)-3,4-dihydro-phthalazin-6-yl]-3-cyclopentyl-propionamide; [M+H]+=444; HPLC r.t. 7.33.

2-Propyl-pentanoic acid [4-oxo-1-(2-trifluoromethyl-benzyl)-3,4-dihydro-phthalazin-6-yl]-amide; [M+H]+=446; HPLC r.t. 7.43.

1-[4-Oxo-1-(2-trifluoromethyl-benzyl)-3,4-dihydro-phthalazin-6-yl]-3-(3-trifluoromethyl-phenyl)-urea; [M+H]+=507; HPLC r.t. 7.36.

1-[4-Oxo-1-(2-trifluoromethyl-benzyl)-3,4-dihydro-phthalazin-6-yl]-3-p-tolyl-urea; [M+H]+=453; HPLC r.t. 6.88.

1-[4-Oxo-1-(2-trifluoromethyl-benzyl)-3,4-dihydro-phthalazin-6-yl]-3-(2,4-difluoro-phenyl)-urea; [M+H]+=475; HPLC r.t. 6.88.

4-(4-Oxo-6-propionylamino-3,4-dihydro-phthalazin-1-ylmethyl)-benzoic acid methyl ester; [M+H]+=366; HPLC r.t. 2.61.

4-[4-Oxo-6-(4-trifluoromethyl-benzoylamino)-3,4-dihydro-phthalazin-1-ylmethyl]-benzoic acid methyl ester; [M+H]+=482; HPLC r.t. 6.47.

4-{6-[(Furan-2-carbonyl)-amino]-4-oxo-3,4-dihydro-phthalazin-1-ylmethyl}-benzoic acid methyl ester; [M+H]+=404; HPLC r.t. 4.91.

4-[6-(3,4-Dimethoxy-benzoylamino)-4-oxo-3,4-dihydro-phthalazin-1-ylmethyl]-benzoic acid methyl ester; [M+H]+=474; HPLC r.t. 5.27.

4-[6-(3-Cyclopentyl-propionylamino)-4-oxo-3,4-dihydro-phthalazin-1-ylmethyl]-benzoic acid methyl ester; [M+H]+=434; HPLC r.t. 6.48.

4-[4-Oxo-6-(2-propyl-pentanoylamino)-3,4-dihydro-phthalazin-1-ylmethyl]-benzoic acid methyl ester; [M+H]+=436; HPLC r.t. 6.61.

4-{6-[3-(3-Methoxy-phenyl)-ureido]-4-oxo-3,4-dihydro-phthalazin-1-ylmethyl}-benzoic acid methyl ester; [M+H]+=459; HPLC r.t. 5.74.

4-[4-Oxo-6-(3-p-tolyl-ureido)-3,4-dihydro-phthalazin-1-ylmethyl]-benzoic acid methyl ester; [M+H]+=443; HPLC r.t. 6.03.

4-{6-[3-(2,4-Difluoro-phenyl)-ureido]-4-oxo-3,4-dihydro-phthalazin-1-ylmethyl}-benzoic acid methyl ester; [M+H]+=465; HPLC r.t. 6.04.

N-[1-(4-Chloro-3-fluoro-benzyl)-4-oxo-3,4-dihydro-phthalazin-6-yl]-propionamide; [M+H]+=360; HPLC r.t. 4.04.

N-[1-(4-Chloro-3-fluoro-benzyl)-4-oxo-3,4-dihydro-phthalazin-6-yl]-4-trifluoromethyl-benzamide; [M+H]+=476; HPLC r.t. 6.3.

Furan-2-carboxylic acid [1-(4-chloro-3-fluoro-benzyl)-4-oxo-3,4-dihydro-phthalazin-6-yl]-amide; [M+H]+=398; HPLC r.t. 4.58.

N-[1-(4-Chloro-3-fluoro-benzyl)-4-oxo-3,4-dihydro-phthalazin-6-yl]-3,4-dimethoxy-benzamide; [M+H]+=468; HPLC r.t. 4.97.

N-[1-(4-Chloro-3-fluoro-benzyl)-4-oxo-3,4-dihydro-phthalazin-6-yl]-3-cyclopentyl-propionamide; [M+H]+=428; HPLC r.t. 7.3.

2-Propyl-pentanoic acid [1-(4-chloro-3-fluoro-benzyl)-4-oxo-3,4-dihydro-phthalazin-6-yl]-amide; [M+H]+=430; HPLC r.t. 7.41.

1-[1-(4-Chloro-3-fluoro-benzyl)-4-oxo-3,4-dihydro-phthalazin-6-yl]-3-(3-trifluoromethyl-phenyl)-urea; [M+H]+=491; HPLC r.t. 6.54.

1-[1-(4-Chloro-3-fluoro-benzyl)-4-oxo-3,4-dihydro-phthalazin-6-yl]-3-p-tolyl-urea; [M+H]+=437; HPLC r.t. 5.91.

N-{1-[(E)-3-(4-Nitro-phenyl)-allyl]-4-oxo-3,4-dihydro-phthalazin-6-yl}-3,4-dimethoxy-benzamide; [M+H]+=; HPLC r.t. 4.96.

N-(4-Oxo-1-thiophen-3-ylmethyl-3,4-dihydro-phthalazin-6-yl)-propionamide; [M+H]+=314; HPLC r.t. 4.26.

N-(4-Oxo-1-thiophen-3-ylmethyl-3,4-dihydro-phthalazin-6-yl)-4-trifluoromethyl-benzamide; [M+H]+=430; HPLC r.t. 6.43.

Furan-2-carboxylic acid (4-oxo-1-thiophen-3-ylmethyl-3,4-dihydro-phthalazin-6-yl)-amide; [M+H]+=352; HPLC r.t. 4.76.

N-(4-Oxo-1-thiophen-3-ylmethyl-3,4-dihydro-phthalazin-6-yl)-3,4-dimethoxy-benzamide; [M+H]+=422; HPLC r.t. 5.16.

2-Propyl-pentanoic acid (4-oxo-1-thiophen-3-ylmethyl-3,4-dihydro-phthalazin-6-yl)-amide; [M+H]+=384; HPLC r.t. 6.54.

1-(4-Oxo-1-thiophen-3-ylmethyl-3,4-dihydro-phthalazin-6-yl)-3-(3-trifluoromethyl-phenyl)-urea; [M+H]+=445; HPLC r.t. 6.57.

1-(4-Oxo-1-thiophen-3-ylmethyl-3,4-dihydro-phthalazin-6-yl)-3-methoxy-phenyl)-urea; [M+H]+=407; HPLC r.t. 5.66.

1-(4-Oxo-1-thiophen-3-ylmethyl-3,4-dihydro-phthalazin-6-yl)-3-p-tolyl-urea; [M+H]+=391; HPLC r.t. 5.98.

1-(4-Oxo-1-thiophen-3-ylmethyl-3,4-dihydro-phthalazin-6-yl)-3-(2,4-difluoro-phenyl)-urea; [M+H]+=413; HPLC r.t. 5.96.

N-[1-(3-Methoxy-benzyl)-4-oxo-3,4-dihydro-phthalazin-6-yl]-propionamide; [M+H]+=338; HPLC r.t. 4.48.

N-[1-(3-Methoxy-benzyl)-4-oxo-3,4-dihydro-phthalazin-6-yl]-4-trifluoromethyl-benzamide; [M+H]+=454; HPLC r.t. 6.52.

Furan-2-carboxylic acid [1-(3-methoxy-benzyl)-4-oxo-3,4-dihydro-phthalazin-6-yl]-amide; [M+H]+=376; HPLC r.t. 4.95.

N-[1-(3-Methoxy-benzyl)-4-oxo-3,4-dihydro-phthalazin-6-yl]-3,4-dimethoxy-benzamide; [M+H]+=446; HPLC r.t. 5.32.

N-[1-(3-Methoxy-benzyl)-4-oxo-3,4-dihydro-phthalazin-6-yl]-3-cyclopentyl-propionamide; [M+H]+=406; HPLC r.t. 6.53.

2-Propyl-pentanoic acid [1-(3-methoxy-benzyl)-4-oxo-3,4-dihydro-phthalazin-6-yl]-amide; [M+H]+=408; HPLC r.t. 6.65; $^1$H-NMR (DMSO-d6), diagnostic signals (ppm): 0.84 (q, 6H), 1.15-1.62 (m, 8H), 2.41 (m, 1H), 3.68 (s, 3H), 4.18 (s, 2H), 6.75 (ddd, 1H), 6.82 (dt, 1H), 6.86 (t, 1H), 7.16 (t, 1H), 7.89 (d, 1H), 7.95 (dd, 1H), 8.55 (d, 1H), 10.34 (s, 1H), 12.41 (s, 1H).

1-[1-(3-Methoxy-benzyl)-4-oxo-3,4-dihydro-phthalazin-6-yl]-3-(3-trifluoromethyl-phenyl)-urea; [M+H]+=469; HPLC r.t. 6.67.

1-[1-(3-Methoxy-benzyl)-4-oxo-3,4-dihydro-phthalazin-6-yl]-(3-methoxy-phenyl)-urea; [M+H]+=431; HPLC r.t. 5.79.

1-[1-(3-Methoxy-benzyl)-4-oxo-3,4-dihydro-phthalazin-6-yl]-3-p-tolyl-urea; [M+H]+=415; HPLC r.t. 6.08.

1-[1-(3-Methoxy-benzyl)-4-oxo-3,4-dihydro-phthalazin-6-yl]-3-(2,4-difluoro-phenyl)-urea; [M+H]+=437; HPLC r.t. 6.08.

N-(4-Oxo-1-propyl-3,4-dihydro-phthalazin-6-yl)-propionamide; [M+H]+=260; HPLC r.t. 3.78.

Furan-2-carboxylic acid (4-oxo-1-propyl-3,4-dihydro-phthalazin-6-yl)-amide; [M+H]+=298; HPLC r.t. 4.35.

1-(4-Oxo-1-propyl-3,4-dihydro-phthalazin-6-yl)-3-p-tolyl-urea; [M+H]+=; HPLC r.t. 5.69.

1-(4-Oxo-1-propyl-3,4-dihydro-phthalazin-6-yl)-3-(2,4-difluoro-phenyl)-urea; [M+H]+=359; HPLC r.t. 5.68.

N-[4-Oxo-1-(3-phenyl-propyl)-3,4-dihydro-phthalazin-6-yl]-propionamide; [M+H]+=336; HPLC r.t. 5.35.

N-[4-Oxo-1-(3-phenyl-propyl)-3,4-dihydro-phthalazin-6-yl]-4-trifluoromethyl-benzamide; [M+H]+=452; HPLC r.t. 7.26.

Furan-2-carboxylic acid [4-oxo-1-(3-phenyl-propyl)-3,4-dihydro-phthalazin-6-yl]-amide; [M+H]+=374; HPLC r.t. 5.78.

N-[4-Oxo-1-(3-phenyl-propyl)-3,4-dihydro-phthalazin-6-yl]-3,4-dimethoxy-benzamide; [M+H]+=444; HPLC r.t. 6.11.

N-[4-Oxo-1-(3-phenyl-propyl)-3,4-dihydro-phthalazin-6-yl]-3-cyclopentyl-propionamide; [M+H]+=404; HPLC r.t. 7.31.

2-Propyl-pentanoic acid [4-oxo-1-(3-phenyl-propyl)-3,4-dihydro-phthalazin-6-yl]-amide; [M+H]+=406; HPLC r.t. 7.43.

1-[4-Oxo-1-(3-phenyl-propyl)-3,4-dihydro-phthalazin-6-yl]-3-(3-trifluoromethyl-phenyl)-urea; [M+H]+=467; HPLC r.t. 7.41.

1-[4-Oxo-1-(3-phenyl-propyl)-3,4-dihydro-phthalazin-6-yl]-(3-methoxy-phenyl)-urea; [M+H]+=429; HPLC r.t. 6.56.

1-[4-Oxo-1-(3-phenyl-propyl)-3,4-dihydro-phthalazin-6-yl]-3-p-tolyl-urea; [M+H]+=413; HPLC r.t. 6.88.

1-[4-Oxo-1-(3-phenyl-propyl)-3,4-dihydro-phthalazin-6-yl]-3-(2,4-difluoro-phenyl)-urea; [M+H]+=435; HPLC r.t. 6.88.

1-[1-(3-Fluoro-benzyl)-4-oxo-3,4-dihydro-phthalazin-6-yl]-3-(2,4-difluoro-phenyl)-urea; [M+H]+=425; $^1$H-NMR (DMSO-d6), diagnostic signals (ppm): 4.25 (s, 2H), 6.97-7.08 (m, 2H), 7.09-7.15 (m, 2H), 7.27-7.35 (m, 2H), 7.77 (dd, 1H), 7.86 (d, 1H), 7.98-8.08 (m, 1H), 8.42 (d, 1H), 8.61 (d, 1H), 9.55 (s, 1H), 12.42 (s, 1H).

1[1-(3-Fluoro-benzyl)-4-oxo-3,4-dihydro-phthalazin-6-yl]-3-p-tolyl-urea; [M+H]+403; $^1$H-NMR (DMSO-d6), diagnostic signals (ppm): 2.23 (s, 3H), 4.24 (s, 2H), 7.00 (m, 1H), 7.05-7.16 (m, 4H), 7.27-7.35 (m, 3H), 7.79 (dd, 1H), 7.84 (d, 1H), 8.39 (d, 1H), 8.70 (br. S, 1H), 9.20 (br. S, 1H), 12.39 (s, 1H).

What is claimed is:

1. An amino-plithalazinone compound represented by formula (I)

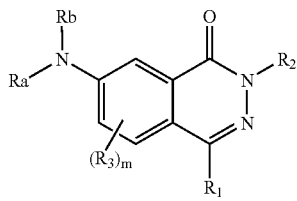

wherein
Ra and Rb are, each independently, a hydrogen atom or a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or one of Ra or Rb is hydrogen or an optionally substituted straight or branched $C_1$-$C_6$ alkyl group, and the other is a group selected from —COR', —CONHR', —COOR' or —SO$_2$R', wherein R' is hydrogen or an optionally substituted group selected from alkyl, cycloalkyl, cycloalkylalkyl, aryl, arylalkyl, heterocyclyl or heterocyclylalkyl, as set forth above;

$R_1$ is a group of formula —CHR$_4$R$_5$ wherein R$_4$ and R$_5$ are, each independently, hydrogen or an optionally substituted group selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_1$ is a group of formula —NHR', —NR'COR", —NR'CONHR" or —NR'SO$_2$R", wherein R' has the above reported meanings other than hydrogen, and R" is hydrogen or has the meanings set forth above for R';

$R_2$ is a hydrogen atom or it is a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur;

any $R_3$, being placed in one or more of the free positions 5, 6 and 8 of the phthalazinone ring are, independently from each other, halogen, nitro, carboxy, cyano or a group optionally further substituted selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyt $C_1$-$C_6$ alkyl with from 1 to 3 hetero atoms selected among nitrogen, oxygen or sulfur; or $R_3$ is a group selected from —COR', —CONHR', —SO$_2$R', —NR'R", —NR'COR", —NR'CONHR' or —NR'SO$_2$R", wherein R' and R" are, the same or different, hydrogen or a group as set forth above;

m is 0 or an integer from 1 to 3;

or a pharmaceutically acceptable salt thereof with the proviso that i) $R_1$ can not be 4-methylpyridine when Ra and Rb are hydrogen and ii) $R_1$ can not be CH$_3$;

the compounds N-[3,4-dihydro-4-oxo-1-(4-pyridinylmethyl)-6-phthalazinyl]-acetamide and N-[3,4-dihydro-4-oxo-1-(4-pyridinylmethyl)-6-phthalazinyl]-2,2,2-trifluoro-acetamide, being excluded.

2. A compound of formula (I) according to claim 1 wherein one of Ra or Rb is a hydrogen atom or an optionally substituted straight or branched $C_1$-$C_6$ alkyl group and the other is a group —COR' wherein R' is an optionally substituted group selected from alkyl, cycloalkyl, cycloalkylalkyl, aryl, arylalkyl, heterocyclyl or heterocyclylalkyl, as defined in claim 1, and $R_1$, $R_2$, $R_3$ and m are as defined in claim 1.

3. A compound of formula (I) according to claim 2 wherein $R_1$ is a —CHR$_4$R$_5$ group and $R_2$ is hydrogen and m is 0.

4. A compound of formula (I) according to claim 1 wherein one of Ra or Rb is a hydrogen atom or an optionally substituted straight or branched $C_1$-$C_6$ alkyl group and the other is a group —CONHR' wherein R' is a hydrogen atom or an optionally substituted group selected from alkyl, cycloalkyl, cycloalkylalkyl, aryl, arylalkyl, heterocyclyl or heterocylylalkyl, as defined in claim 1, and $R_1$, $R_2$, $R_3$ and m are as defined in claim 1.

5. A compound of formula (I) according to claim 4 wherein $R_1$ is a —CHR$_4$R$_5$ group and $R_2$ is hydrogen and m is 0.

6. A compound of fonnula (I) according to claim 1 wherein one of Ra or Rb is a hydrogen atom or an optionally substituted straight or branched $C_1$-$C_6$ alkyl group and the other is a group —COOR' wherein R' is a hydrogen atom or an optionally substituted group selected from alkyl, cycloalkyl, cycloalkylalkyl, aryl, arylalkyl, heterocyclyl or heterocylylalkyl, as defined in claim 1, and $R_1$, $R_2$, $R_3$ and m are as defined in claim 1.

7. A compound of formula (I) according to claim 6 wherein $R_1$ is a —CHR$_4$R$_5$ group and $R_2$ is hydrogen and m is 0.

8. A compound of formula (I) according to claim 1 wherein one of Ra or Rb is a hydrogen atom or an optionally substituted straight or branched $C_1$-$C_6$ alkyl group and the other is a group —SO$_2$R' wherein R' is an optionally substituted group selected from alkyl, cycloalkyl, cycloalkylalkyl, aryl, arylalkyl, heterocyclyl or heterocyclylalkyl, as defined in claim 1, and $R_1$, $R_2$, $R_3$ and mare as defined in claim 1.

9. A compound of formula (I) according to claim 8 wherein $R_1$ is a —CHR$_4$R$_5$ group and $R_2$ is hydrogen and m is 0.

10. A compound of formula (I) according to claim 1 wherein Ra and Rb are both hydrogen atoms and $R_1$, $R_2$, $R_3$ and m are as defined in claim 1.

11. A compound of formula (I) according to claim 10 wherein $R_1$ is a —CHR$_4$R$_5$ group and $R_2$ is hydrogen and m is 0.

12. A compound of formula (I) according to claim 1 wherein one of Ra or Rb is a hydrogen atom or an optionally substituted straight or branched $C_1$-$C_6$ alkyl and the other is a group, optionally further substituted, selected from alkyl, cycloalkylalkyl, arylalkyl or heterocyclylalkyl as defined in claim 1, and $R_1$, $R_2$, $R_3$ and m are as defined in claim 1.

13. A compound of formula (I) according to claim 12 wherein $R_1$ is a group —CHR$_4$R$_5$ wherein R$_4$ and R$_5$ are as above defined, $R_2$ is hydrogen and m is 0.

14. A compound of formula (I) as defined in claim 1, optionally in the form of a pharmaceutically acceptable salt, selected from:
 1. 4-(4-Oxo-6-propionylamino-3,4-dihydro-phthalazin-1-ylmethyl)-benzoic acid methyl ester;
 2. 4-[4-Oxo-6-(4-trifluoromethyl-benzoylamino)-3,4-dihydro-phthalazin-1-ylmethyl]-benzoic acid methyl ester;
 3. 4-{6-[(Furan-2-carbonyl)-amino]-4-oxo-3,4-dihydrophthalazin-1-ylmethyl}-benzoic acid methyl ester;

4. 4-[6-(3,4-Dimethoxy-benzoylamino)-4-oxo-3,4-dihydro-phthalazin-1-ylmethyl]-benzoic acid methyl ester;
5. 4-[6-(3-Cyclopentyl-propionylamino)-4-oxo-3,4-dihydro-phthalazin-1-ylmethyl]-benzoic acid methyl ester;
6. 4-[4-Oxo-6-(2-propyl-pentanoylamino)-3,4-dihydro-phthalazin-1-ylmethyl]-benzoic acid methyl ester;
7. 4-{4-Oxo-6-[3-(3-trifluoromethyl-phenyl)-ureido]-3,4-dihydro-phthalazin-1-ylmethyl}-benzoic acid methyl ester;
8. 4-{6-[3-(3-Methoxy-phenyl)-ureido]-4-oxo-3,4-dihydro-phthalazin-1-ylmethyl)-benzoic acid methyl ester;
9. 4-[4-Oxo-6-(3-p-tolyl-ureido)-3,4-dihydro-phthalazin-1-ylmethyl]-benzoic acid methyl ester;
10. 4-{6-[3-(2,4-Difluoro-phenyl)-ureido]-4-oxo-3,4-dihydro-phthalazin-1-ylmethyl}-benzoic acid methyl ester;
11. 4-{6-[3-(3,4-Dichloro-phenyl)-ureido]-4-oxo-3,4-dihydro-phthalazin-1-ylmethyl}-benzoic acid methyl ester;
12. 4-[4-Oxo-6-(3-pyridin-3-yl-ureido)-3-4-dihydro-phthalazin-1-ylmethyl]-benzoic acid methyl ester;
13. 4-(6-Amino-4-oxo-3,4-dihydro-phthalazin-1-ylmethyl)-benzoic acid methyl ester;
14. N-[1-(4-Chloro-3-fluoro-benzyl)-4-oxo-3,4-dihydro-phthalazin-6-yl]-propionamide;
15. N-[1-[4-Chloro-3-fluoro-benzyl)-4-oxo-3,4-dihydro-phthalazin-6-yl]-4-trifluoromethyl benzamide;
16. Furan-2-carboxylic acid [1-(4-chloro-3-fluoro-benzyl)-4-oxo-3,4-dihydro-phthalazin-6-yl]-amide;
17. N-[1-(4-Chloro-3-fluoro-benzyl)-4-oxo-3-4-dihydro-phthalazin-6-yl]-3-4-dimethoxy-benzamide;
18. N-[1-(4-Chloro-3-fluoro-benzyl)-4-oxo-3,4-dihydro-phthalazin-6-yl]-3-cyclopentyl-propionamide;
19. 2-Propyl-pentanoic acid [1-(4-chloro-3-fluoro-benzyl)-4-oxo-3,4-dihydro-phthalazin-6-yl]-amide;
20. 1-[1-(4-Chloro-3-fluoro-benzyl)-4-oxo-3,4-dihydro-phthalazin-6-yl]-3-(3-trifluoromethyl-phenyl)-urea;
21. 1-[1-(4-Chloro-3-fluoro-benzyl)-4-oxo-3,4-dihydro-phthalazin-6-yl]-3-(3-methoxy-phenyl)-urea;
22. 1-[1-(4-Chloro-3-fluoro-benzyl)-4-oxo-3,4-dihydro-phthalazin-6-yl]-3-p-tolyl-urea;
23. 1-[1-(4-Chloro-3-fluoro-benzyl)-4-oxo-3,4-dihydro-phthalazin-6-yl]-3-(2,4-difluoro-phenyl)-urea;
24. 1-[1-(4-Chloro-3-fluoro-benzyl)-4-oxo-3,4-dihydro-phthalazin-6-yl]-3-(3,4-dichloro-phenyl)-urea;
25. 1-[1-(4-Chloro-3-fluoro-benzyl)-4-oxo-3,4-dihydro-phthalazin-6-yl]-3-pyridin-3-yl-urea;
26. 7-Amino-4-(4-chloro-3-fluoro-benzyl)-2H-phthalazin-1-one;
27. N-{1-[(E)-3-(4-Nitro-phenyl)-allyl]-4-oxo-3,4-dihydro-phthalazin-6-yl}-propionamide;
28. N-{1-[(E)-3-(4-Nitro-phenyl)-allyl]-4-oxo-3,4-dihydro-phthalazin-6-yl}-4-trifluoromethyl-benzamide;
29. Furan-2-carboxylic acid {1-[(E)-3-(4-nitro-phenyl)-allyl]-4-oxo-3,4-dihydro-phthalazin-6-yl}-amide;
30. N-{1-[(E)-3-(4-Nitro-phenyl)-allyl]-4-oxo-3,4-dihydro-phthalazin-6-yl}-3,4-dimethoxy benzamide;
31. N-{1-[(E)-3-(4-Nitro-phenyl)-allyl]-4-oxo-3,4-dihydro-phthalazin-6-yl}-3-cyclopentyl-propionamide;
32. 2-Propyl-pentanoic acid {1-[(E)-3-(4-nitro-phenyl)-allyl]-4-oxo-3,4-dihydro-phthalazin-6-yl}-amide;
33. 1-{1-[(E)-3-(4-Nitro-phenyl)-allyl]-4-oxo-3,4-dihydro-phthalazin-6-yl}-3-(3-trifluoromethyl-phenyl)-urea;
34. 1-{1-[(E)-3-(4-Nitro-phenyl)-allyl]-4-oxo-3,4-dihydro-phthalazin-6-yl}-(3-methoxy-phenyl)-urea;
35. 1-1-((E)-3-(4-Nitro-phenyl)-allyl]-4-oxo-3,4-dihydro-phthalazin-6-yl}-3-p-tolyl-urea;
36. 1-{1-[(E)-3-(4-Nitro-phenyl)-allyl]-4-oxo-3,4-dihydro-phthalazin-6-yl}-3-(2,4-difluoro-phenyl)-urea;
37. 1-{1-[(E)-3-(4-Nitro-phenyl)-allyl]-4-oxo-3,4-dihydro-phthalazin-6-yl}-3-(3,4-dichloro-phenyl)-urea;
38. 1-{1-[(E)-3-(4-Nitro-phenyl)-allyl]-4-oxo-3,4-dihydro-phthalazin-6-yl}-3-pyridin-3-yl-urea;
39. 7-Amino-4-[(E)-3-(4-nitro-phenyl)-allyl]-2H-phthalazin-1-one;
40. N-(4-Oxo-1-thiophen-3-ylmethyl-3,4-dihydro-phthalazin-6-yl)-propionamide;
41. N-(4-Oxo-1-thiophen-3-ylmethyl-3,4-dihydro-phthalazin-6-yl)-4-trifluoromethyl benzamide;
42. Furan-2-carboxylic acid (4-oxo-1-thiophen-3-ylmethyl-3,4-dihydro-phthalazin-6-yl)-amide;
43. N-(4-Oxo-1-thiophen-3-ylmethyl-3,4-dihydro-phthalazin-6-yl)-3,4-dimethoxy benzamide;
44. N-(4-Oxo-1-thiophen-3-ylmethyl-3,4-dihydro-phthalazin-6-yl)-3-cyclopentyl propionamide;
45. 2-Propyl-pentanoic acid (4-oxo-1-thiophen-3-ylmethyl-3,4-dihydro-phthalazin-6-yl)-amide;
46. 1-(4-Oxo-1-thiophen-3-ylmethyl-3,4-dihydro-phthalazin-6-yl)-3-(3-trifluoromethyl-phenyl)-urea;
47. 1-(4-Oxo-1-thiophen-3-ylmethyl-3,4-dihydro-phthalazin-6-yl)-(3-methoxy-phenyl)-urea;
48. 1-(4-Oxo-1-thiophen-3-ylmethyl-3,4-dihydro-phthalazin-6-yl)-3-p-tolyl-urea;
49. 1-(4-Oxo-1-thiophen-3-ylmethyl-3,4-dihydro-phthalazin-6-yl)-3-(2,4-difluoro-phenyl)-urea;
50. 1-(4-Oxo-1-thiophen-3-ylmethyl-3,4-dihydro-phthalazin-6-yl)-3-(3,4-dichloro-phenyl)-urea;
51. 1-(4-Oxo-1-thiophen-3-ylmethyl-3,4-dihydro-phthalazin-6-yl)-3-pyridin-3-yl-urea;
52. 7-Amino-4-thiophen-3-ylmethyl-2H-phthalazin-1-one;
53. N-[1-(3-Methoxy-benzyl)-4-oxo-3,4-dihydro-phthalazin-6-yl]-propionamide;
54. N-[1-(3-Methoxy-benzyl)-4-oxo-3,4-dihydro-phthalazin-6-yl]-4-trifluoromethyl benzamide; 55. Furan-2-carboxylic acid [1-(3-methoxy-benzyl)-4-oxo-3,4-dihydro-phthalazin-6-yl]-amide;
56. N-[1-(3-Methoxy-benzyl)-4-oxo-3,4-dihydro-phthalazin-6-yl]-3,4-dimethoxy benzamide;
57. N-[1-(3-Methoxy-benzyl)-4-oxo-3,4-dihydro-phthalazin-6-yl]-3-cyclopentyl propionamide;
58. 2-Propyl-pentanoic acid [1-(3-methoxy-benzyl)-4-oxo-3,4-dihydro-phthalazin-6-yl]-amide;
59. 1-[1-(3-Methoxy-benzyl)-4-oxo-3,4-dihydro-phthalazin-6-yl]-3-(3-trifluoromethyl-phenyl)-urea;
60. 1-[1-(3-Methoxy-benzyl)-4-oxo-3,4-dihydro-phthalazin-6-yl]-(3-methoxy-phenyl)-urea;
61. 1-[1-(3-Methoxy-benzyl)-4-oxo-3,4-dihydro-phthalazin-6-yl]-3-p-tolyl urea;
62. 1-[1-(3-Methoxy-benzyl)-4-oxo-3,4-dihydro-phthalazin-6-yl]-3-(2,4-difluoro-phenyl)-urea;
63. 1-[1-(3-Methoxy-benzyl)-4-oxo-3,4-dihydro-phthalazin-6-yl]-3-(3,4-dichloro-phenyl)-urea;
64. 1-[1-(3-Methoxy-benzyl)-4-oxo-3,4-dihydro-phthalazin-6-yl]-3-pyridin-3-yl-urea;
65. 7-Amino-4-(3-methoxy-benzyl)-2H-phthalazin-1-one;
66. N-(4-Oxo-1-propyl-3,4-dihydro-phthalazin-6-yl)-propionamide;
67. N-(4-Oxo-1-propyl-3,4-dihydro-phthalazin-6-yl)-4-trifluoromethyl-benzamide;

68. Furan-2-carboxylic acid (4-oxo-1-propyl-3,4-dihydro-phthalazin-6-yl)-amide;
69. N-(4-Oxo-1-propyl-3,4-dihydro-phthalazin-6-yl)-3,4-dimethoxy benzamide;
70. N-(4-Oxo-1-propyl-3,4-dihydro-phthalazin-6-yl)-3-cyclopentyl-propionamide;
71. 2-Propyl-pentanoic acid (4-oxo-1-propyl-3,4-dihydro-phthalazin-6-yl)-amide;
72. 1-(4-Oxo-1-propyl-3,4-dihydro-phthalazin-6-yl)-3-(3-trifluoromethyl-phenyl)-urea;
73. 1-(4-Oxo-1-propyl-3,4-dihydro-phthalazin-6-yl)-(3-methoxy-phenyl)-urea;
74. 1-(4-Oxo-1-propyl-3,4-dihydro-phthalazin-6-yl)-3-p-tolyl urea;
75. 1-(4-Oxo-1-propyl-3,4-dihydro-phthalazin-6-yl)-3-(2,4-difluoro-phenyl)-urea;
76. 1-(4-Oxo-1-propyl-3,4-dihydro-phthalazin-6-yl)-3-(3,4-dichloro-phenyl)-urea;
77. 1-(4-Oxo-1-propyl-3,4-dihydro-phthalazin-6-yl)-3-pyridin-3-yl-urea;
78. 7-Amino-4-propyl-2H-phthalazin-1-one;
79. N-[1-(3,3-Dimethyl-butyl)-4-oxo-3,4-dihydro-phthalazin-6-yl]-propionamide;
80. N-[1-(3,3-Dimethyl-butyl)-4-oxo-3,4-dihydro-phthalazin-6-yl]-4-trifluoromethyl benzamide;
81. Furan-2-carboxylic acid [1-(3,3-dimethyl-butyl)-4-oxo-3,4-dihydro-phthalazin-6-yl]-amide;
82. N-[1-(3,3-Dimethyl-butyl)-4-oxo-3,4-dihydro-phthalazin-6-yl]-3,4-dimethoxy benzamide;
83. N-[1-(3,3-Dimethyl-butyl)-4-oxo-3,4-dihydro-phthalazin-6-yl]-3-cyclopentyl propionamide;
84. 2-Propyl-pentanoic acid [1-(3,3-dimethyl-butyl)-4-oxo-3,4-dihydro-phthalazin-6-yl]-amide;
85. 1-[1-(3,3-Dimethyl-butyl)-4-oxo-3,4-dihydro-phthalazin-6-yl]-3-(3-trifluoromethyl-phenyl)-urea;
86. 1-[1-(3,3-Dimethyl-butyl)-4-oxo-3,4-dihydro-phthalazin-6-yl]-(3-methoxy-phenyl)-urea;
87. 1-[1-(3,3-Dimethyl-butyl)-4-oxo-3,4-dihydro-phthalazin-6-yl]-3-p-tolyl urea;
88. 1-[1-(3,3-Dimethyl-butyl)-4-oxo-3,4-dihydro-phthalazin-6-yl]-3-(2,4-difluoro-phenyl)-urea;
89. 1-[1-(3,3-Dimethyl-butyl)-4-oxo-3,4-dihydro-phthalazin-6-yl]-3-(3,4-dichloro-phenyl)-urea;
90. 1-[1-(3,3-Dimethyl-butyl)-4-oxo-3,4-dihydro-phthalazin-6-yl]-3-pyridin-3-yl-urea;
91. 7-Amino-4-(3,3-dimethyl-butyl)-2H-phthalazin-1-one;
92. N-[4-Oxo-1-(3-phenyl-propyl)-3,4-dihydro-phthalazin-6-yl]-propionamide;
93. N-[4-Oxo-1-(3-phenyl-propyl)-3,4-dihydro-phthalazin-6-yl]-4-trifluoromethyl benzamide;
94. Furan-2-carboxylic acid [4-oxo-1-(3-phenyl-propyl)-3,4-dihydro-phthalazin-6-yl]-amide;
95. N-[4-Oxo-1-(3-phenyl-propyl)-3,4-dihydro-phthalazin-6-yl]-3,4-dimethoxy benzamide;
96. N-[4-Oxo-1-(3-phenyl-propyl)-3,4-dihydro-phthalazin-6-yl]-3-cyclopentyl propionamide;
97. 2-Propyl-pentanoic acid [4-oxo-1-(3-phenyl-propyl)-3,4-dihydro-phthalazin-6-yl]-amide;
98. 1-[4-Oxo-1-(3-phenyl-propyl)-3,4-dihydro-phthalazin-6-yl]-3-(3-trifluoromethyl-phenyl)-urea;
99. 1-[4-Oxo-1-(3-phenyl-propyl)-3,4-dihydro-phthalazin-6-yl]-(3-methoxy-phenyl)-urea;
100. 1-[4-Oxo-1-(3-phenyl-propyl)-3,4-dihydro-phthalazin-6-yl]-3-p-tolyl urea;
101. 1-[4-Oxo-1-(3-phenyl-propyl)-3,4-dihydro-phthalazin-6-yl]-3-(2,4-difluoro-phenyl)-urea;
102. 1-[4-Oxo-1-(3-phenyl-propyl)-3,4-dihydro-phthalazin-6-yl]-3-(3,4-dichloro-phenyl)-urea;
103. 1-[4-Oxo-1-(3-phenyl-propyl)-3,4-dihydro-phthalazin-6-yl]-3-pyridin-3-yl-urea;
104. 7-Amino-4-(3-phenyl-propyl)-2H-phthalazin-1-one;
105. N-(4-Oxo-1-pyridin-3-ylmethyl-3,4-dihydro-phthalazin-6-yl)-propionamide;
106. N-(4-Oxo-1-pyridin-3-ylmethyl-3,4-dihydro-phthalazin-6-yl)-4-trifluoromethyl benzamide;
107. Furan-2-carboxylic acid (4-oxo-1-pyridin-3-ylmethyl-3,4-dihydro-phthalazin-6-yl)-amide;
108. N-(4-Oxo-1-pyridin-3-ylmethyl-3,4-dihydro-phthalazin-6-yl)-succinamic acid ethyl ester;
109. N-(4-Oxo-1-pyridin-3-ylmethyl-3,4-dihydro-phthalazin-6-yl)-3-cyclopentyl propionamide;
110. 2-Propyl-pentanoic acid (4-oxo-1-pyridin-3-ylmethyl-3,4-dihydro-phthalazin-6-yl)-amide;
111. 1-(4-Oxo-1-pyridin-3-ylmethyl-3,4-dihydro-phthalazin-6-yl)-3-(3-trifluoromethyl-phenyl)-urea; 112. 1-(3-Methoxy-phenyl)-3-(4-oxo-1-pyridin-3-ylmethyl-3,4-dihydro-phthalazin-6-yl)-urea;
113. 1-(4-Oxo-1-pyridin-3-ylmethyl-3,4-dihydro-phthalazin-6-yl)-3-p-tolyl urea;
114. 1-(2,4-Difluoro-phenyl)-3-(4-oxo-1-pyridin-3-ylmethyl-3,4-dihydro-phthalazin-6-yl)-urea;
115. 1-(3,4-Dichloro-phenyl)-3-(4-oxo-1-pyridin-3-ylmethyl-3,4-dihydro-phthalazin-6-yl)-urea;
116. 1-(4-Oxo-1-pyridin-3-ylmethyl-3,4-dihydro-phthalazin-6-yl)-3-pyridin-3-yl-urea;
117. 7-Amino-4-pyridin-3-ylmethyl-2H-phthalazin-1-one;
118. N-(4-Oxo-1-pyridin-3-ylmethyl-3,4-dihydro-phthalazin-6-yl)-benzamide;
119. N-[1-(4-Chloro-benzyl)-4-oxo-3,4-dihydro-phthalazin-6-yl]-propionamide;
120. N-[1-(4-Chloro-benzyl)-4-oxo-3,4-dihydro-phthalazin-6-yl]-4-trifluoromethyl benzamide;
121. Furan-2-carboxylic acid [1-(4-chloro-benzyl)-4-oxo-3,4-dihydro-phthalazin-6-yl]-amide;
122. N-[1-(4-Chloro-benzyl)-4-oxo-3,4-dihydro-phthalazin-6-yl]-succinamic acid ethyl ester;
123. N-[1-(4-Chloro-benzyl)-4-oxo-3,4-dihydro-phthalazin-6-yl]-3-cyclopentyl propionamide;
124. 2-Propyl-pentanoic acid [1-(4-chloro-benzyl)-4-oxo-3,4-dihydro-phthalazin-6-yl]-amide;
125. 1-[1-(4-Chloro-benzyl)-4-oxo-3,4-dihydro-phthalazin-6-yl]-3-(3-trifluoromethyl-phenyl)-urea;
126. 1-[1-(4-Chloro-benzyl)-4-oxo-3,4-dihydro-phthalazin-6-yl]-3-(3-methoxy-phenyl)-urea;
127. 1-[1-(4-Chloro-benzyl)-4-oxo-3,4-dihydro-phthalazin-6-yl]-3-p-tolyl urea;
128. 1-[1-(4-Chloro-benzyl)-4-oxo-3,4-dihydro-phthalazin-6-yl]-3-(2,4-difluoro-phenyl)-urea;
129. 1-[1-(4-Chloro-benzyl)-4-oxo-3,4-dihydro-phthalazin-6-yl]-3-(3,4-dichloro-phenyl)-urea;
130. 1-[1-(4-Chloro-benzyl)-4-oxo-3,4-dihydro-phthalazin-6-yl]-3-pyridin-3-yl-urea;
131. 7-Amino-4-(4-Chloro-benzyl)-2H-phthalazin-1-one;
132. N-[1-(4-Cyano-benzyl)-4-oxo-3,4-dihydro-phthalazin-6-yl]-propionamide;
133. N-[1-(4-Cyano-benzyl)-4-oxo-3,4-dihydro-phthalazin-6-yl]-4-trifluoromethyl-benzamide;
134. Furan-2-carboxylic acid [1-(4-cyano-benzyl)-4-oxo-3,4-dihydro-phthalazin-6-yl]-amide;
135. N-[1-(4-Cyano-benzyl)-4-oxo-3,4-dihydro-phthalazin-6-yl]-succinamic acid ethyl ester;
136. N-[1-(4-Cyano-benzyl)-4-oxo-3,4-dihydro-phthalazin-6-yl]-3-cyclopentyl propionamide;

137. 2-Propyl-pentanoic acid [1-(4-cyano-benzyl)-4-oxo-3,4-dihydro-phthalazin-6-yl]-amide;
138. 1-[1-(4-Cyano-benzyl)-4-oxo-3,4-dihydro-phthalazin-6-yl]-3-(3-trifluoromethyl-phenyl)-urea;
139. 1-[1-(4-Cyano-benzyl)-4-oxo-3,4-dihydro-phthalazin-6-yl]-3-(3-methoxy-phenyl)-urea;
140. 1-[1-(4-Cyano-benzyl)-4-oxo-3,4-dihydro-phthalazin-6-yl]-3-p-tolyl urea;
141. 1-[1-(4-Cyano-benzyl)-4-oxo-3,4-dihydro-phthalazin-6-yl]-3-(2,4-difluoro-phenyl)-urea;
142. 1-[1-(4-Cyano-benzyl)-4-oxo-3,4-dihydro-phthalazin-6-yl]-3-(3,4-dichloro-phenyl)-urea;
143. 1-[1-(4-Cyano-benzyl)-4-oxo-3,4-dihydro-phthalazin-6-yl]-3-pyridin-3-yl-urea;
144. 7-Amino-4-(4-Cyano-benzyl)-2H-phthalazin-1-one;
145. N-[1-(3-Fluoro-benzyl)-4-oxo-3,4-dihydro-phthalazin-6-yl]-propionamide;
146. N-[1-(3-Fluoro-benzyl)-4-oxo-3,4-dihydro-phthalazin-6-yl]-4-trifluoromethyl benzamide;
147. Furan-2-carboxylic acid [1-(3-fluoro-benzyl)-4-oxo-3,4-dihydro-phthalazin-6-yl]-amide;
148. N-[1-(3-Fluoro-benzyl)-4-oxo-3,4-dihydro-phthalazin-6-yl]-succinamic acid ethyl ester;
149. N-[1-(3-Fluoro-benzyl)-4-oxo-3,4-dihydro-phthalazin-6-yl]-3-cyclopentyl propionamide;
150. 2-Propyl-pentanoic acid [1-(3-fluoro-benzyl)-4-oxo-3,4-dihydro-phthalazin-6-yl]-amide;
151. 1-[1-(3-Fluoro-benzyl)-4-oxo-3,4-dihydro-phthalazin-6-yl]-3-(3-trifluoromethyl-phenyl)-urea;
152. 1-[1-(3-Fluoro-benzyl)-4-oxo-3,4-dihydro-phthalazin-6-yl]-3-(3-methoxy-phenyl)-urea;
153. 1-[1-(3-Fluoro-benzyl)-4-oxo-3,4-dihydro-phthalazin-6-yl]-3-p-tolyl-urea;
154. 1-[1-(3-Fluoro-benzyl)-4-oxo-3,4-dihydro-phthalazin-6-yl]-3-(2,4-difluoro-phenyl)-urea;
155. 1-[1-(3-Fluoro-benzyl)-4-oxo-3,4-dihydro-phthalazin-6-yl]-3-(3,4-dichloro-phenyl)-urea;
156. 1-[1-(3-Fluoro-benzyl)-4-oxo-3,4-dihydro-phthalazin-6-yl]-3-pyridin-3-yl-urea;
157. 7-Amino-4-(3-Fluoro-benzyl)-2H-phthalazin-1-one;
158. N-[1-(3-Methyl-benzyl)-4-oxo-3,4-dihydro-phthalazin-6-yl]-propionamide;
159. N-[1-(3-Methyl-benzyl)-4-oxo-3,4-dihydro-phthalazin-6-yl]-4-trifluoromethyl benzamide;
160. Furan-2-carboxylic acid [1-(3-methyl-benzyl)-4-oxo-3,4-dihydro-phthalazin-6-yl]-amide;
161. N-[1-(3-Methyl-benzyl)-4-oxo-3,4-dihydro-phthalazin-6-yl]-succinamic acid ethyl ester;
162. N-[1-(3-Methyl-benzyl)-4-oxo-3,4-dihydro-phthalazin-6-yl]-3-cyclopentyl propionamide;
163. 2-Propyl-pentanoic acid [1-(3-methyl-benzyl)-4-oxo-3,4-dihydro-phthalazin-6-yl]-amide;
164. 1-[1-(3-Methyl-benzyl)-4-oxo-3,4-dihydro-phthalazin-6-yl]-3-(3-trifluoromethyl-phenyl)-urea;
165. 1-[1-(3-Methyl-benzyl)-4-oxo-3,4-dihydro-phthalazin-6-yl]-3-(3-methoxy-phenyl)-urea;
166. 1-[1-(3-Methyl-benzyl)-4-oxo-3,4-dihydro-phthalazin-6-yl]-3-p-tolylurea;
167. 1-[1-(3-Methyl-benzyl)-4-oxo-3,4-dihydro-phthalazin-6-yl]-3-(2,4-difluoro-phenyl)-urea;
168. 1-[1-(3-Methyl-benzyl)-4-oxo-3,4-dihydro-phthalazin-6-yl]-3-(3,4-dichloro-phenyl)-urea;
169. 1-[1-(3-Methyl-benzyl)-4-oxo-3,4-dihydro-phthalazin-6-yl]-3-pyridin-3-yl-urea;
170. 7-Amino-4-(3-Methyl-benzyl)-2H-phthalazin-1-one;
171. N-[1-(2,4-Dichloro-benzyl)-4-oxo-3,4-dihydro-phthalazin-6-yl]-propionamide;
172. N-[1-(2,4-Dichloro-benzyl)-4-oxo-3,4-dihydro-phthalazin-6-yl]-4-trifluoromethyl-benzamide;
173. Furan-2-carboxylic acid [1-(2,4-dichloro-benzyl)-4-oxo-3,4-dihydro-phthalazin-6-yl]-amide;
174. N-[1-(2,4-Dichloro-benzyl)-4-oxo-3,4-dihydro-phthalazin-6-yl]-succinamic acid ethyl ester;
175. N-[1-(2,4-Dichloro-benzyl)-4-oxo-3,4-dihydro-phthalazin-6-yl]-3-cyclopentyl propionamide;
176. 2-Propyl-pentanoic acid [1-(2,4-dichloro-benzyl)-4-oxo-3,4-dihydro-phthalazin-6-yl]-amide;
177. 1-[1-(2,4-Dichloro-benzyl)-4-oxo-3,4-dihydro-phthalazin-6-yl]-3-(3-trifluoromethyl-phenyl)-urea;
178. 1-[1-(2,4-Dichloro-benzyl)-4-oxo-3,4-dihydro-phthalazin-6-yl]-3-(3-methoxy-phenyl)-urea;
179. 1-[1-(2,4-Dichloro-benzyl)-4-oxo-3,4-dihydro-phthalazin-6-yl]-3-p-tolylurea;
180. 1-[1-(2,4-Dichloro-benzyl)-4-oxo-3,4-dihydro-phthalazin-6-yl]-3-(2,4-difluoro-phenyl)-urea;
181. 1-[1-(2,4-Dichloro-benzyl)-4-oxo-3,4-dihydro-phthalazin-6-yl]-3-(3,4-dichloro-phenyl)-urea;
182. 1-[1-(2,4-Dichloro-benzyl)-4-oxo-3,4-dihydro-phthalazin-6-yl]-3-pyridin-3-yl-urea;
183. 7-Amino-4-(2,4-dichloro-benzyl)-2H-phthalazin-1-one;
184. N-(4-Oxo-1-quinolin-3-ylmethyl-3,4-dihydro-phthalazin-6-yl)-propionamide;
185. N-(4-Oxo-1-quinolin-3-ylmethyl-3,4-dihydro-phthalazin-6-yl)-4-trifluoromethyl-benzamide;
186. Furan-2-carboxylic acid (4-oxo-1-quinolin-3-ylmethyl-3,4-dihydro-phthalazin-6-yl)-amide;
187. N-(4-Oxo-1-quinolin-3-ylmethyl-3,4-dihydro-phthalazin-6-yl)-succinamic acid ethyl ester;
188. N-(4-Oxo-1-quinolin-3-ylmethyl-3,4-dihydro-phthalazin-6-yl)-3-cyclopentyl propionamide;
189. 2-Propyl-pentanoic acid (4-oxo-1-quinolin-3-ylmethyl-3,4-dihydro-phthalazin-6-yl)-amide;
190. 1-(4-Oxo-1-quinolin-3-ylmethyl-3,4-dihydro-phthalazin-6-yl)-3-(3-trifluoromethyl-phenyl)-urea;
191. 1-(4-Oxo-1-quinolin-3-ylmethyl-3,4-dihydro-phthalazin-6-yl)-3-(3-methoxy-phenyl)-urea;
192. 1-(4-Oxo-1-quinolin-3-ylmethyl-3,4-dihydro-phthalazin-6-yl)-3-p-tolyl urea;
193. 1-(4-Oxo-1-quinolin-3-ylmethyl-3,4-dihydro-phthalazin-6-yl)-3-(2,4-difluoro-phenyl)-urea;
194. 1-(4-Oxo-1-quinolin-3-ylmethyl-3,4-dihydro-phthalazin-6-yl)-3-(3,4-dichloro-phenyl)-urea;
195. 1-(4-Oxo-1-quinolin-3-ylmethyl-3,4-dihydro-phthalazin-6-yl)-3-pyridin-3-yl-urea;
196. 7-Amino-4-quinolin-3-ylmethyl-2H-phthalazin-1-one;
197. N-[4-Oxo-1-(2-trifluoromethyl-benzyl)-3,4-dihydro-phthalazin-6-yl]-propionamide;
198. N-[4-Oxo-1-(2-trifluoromethyl-benzyl)-3,4-dihydro-phthalazin-6-yl]-4-trifluoromethyl benzamide;
199. Furan-2-carboxylic acid [4-oxo-1-(2-trifluoromethyl-benzyl)-3,4-dihydro-phthalazin-6-yl]-amide;
200. N-[4-Oxo-1-(2-trifluoromethyl-benzyl)-3,4-dihydro-phthalazin-6-yl]-succinamic acid ethyl ester;
201. N-[4-Oxo-1-(2-trifluoromethyl-benzyl)-3,4-dihydro-phthalazin-6-yl]-3-cyclopentyl propionamide;
202. 2-Propyl-pentanoic acid [4-oxo-1-(2-trifluoromethyl-benzyl)-3,4-dihydro-phthalazin-6-yl]-amide;
203. 1-[4-Oxo-1-(2-trifluoromethyl-benzyl)-3,4-dihydro-phthalazin-6-yl]-3-(3-trifluoromethyl-phenyl)-urea;
204. 1-[4-Oxo-1-(2-trifluoromethyl-benzyl)-3,4-dihydro-phthalazin-6-yl]-3-(3-methoxy-phenyl)-urea;

205. 1-[4-Oxo-1-(2-trifluoromethyl-benzyl)-3,4-dihydro-phthalazin-6-yl]-3-p-tolyl urea;
206. 1-[4-Oxo-1-(2-trifluoromethyl-benzyl)-3,4-dihydro-phthalazin-6-yl]-3-(2,4-difluoro-phenyl)-urea;
207. 1-[4-Oxo-1-(2-trifluoromethyl-benzyl)-3,4-dihydro-phthalazin-6-yl]-3-(3,4-dichloro-phenyl)-urea;
208. 1-[4-Oxo-1-(2-trifluoromethyl-benzyl)-3,4-dihydro-phthalazin-6-yl]-3-pyridin-3-yl-urea;
209. 7-Amino-4-(2-trifluoromethyl-benzyl)-2H-phthalazin-1-one.

15. A process for preparing the compounds of formula (I) as defined in claim 1, and the pharmaceutically acceptable salts thereof, which process comprises:

a) reacting a compound of formula (II)

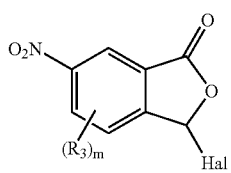
(II)

wherein $R_3$ and m are as defined in claim 1 and Hal represents a halogen atom, with a suitable phosphine compound ($PL_3$), under optional reductive conditions, so as to obtain a compound of formula (III)

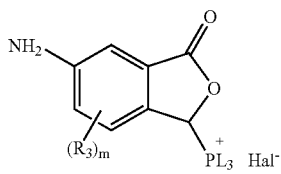
(III)

wherein P is a phosphorus atom and L are the phosphine ligands;

b) reacting the compound of formula (III) with an aldehydic Resin-CHO, in the presence of a suitable reducing agent, so as to obtain a resin supported compound of formula (IV)

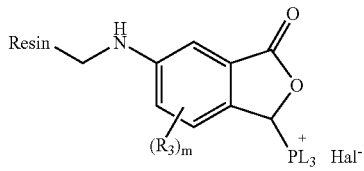
(IV)

c) reacting the compound of formula (IV) with a carbonyl compound of formula (V) or a nitroso compound of formula (VI)

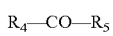 (V)

 (VI)

wherein $R_4$, $R_5$ and R' are as defined in claim 1; so as to obtain the compound of formula (VII)

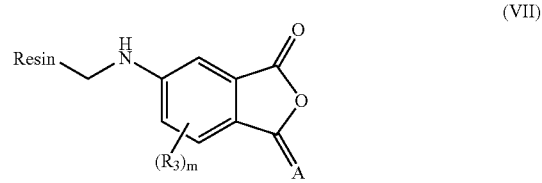
(VII)

wherein A is a group $=CR_4R_5$ or $=NR'$, respectively; and optionally reacting the compound of
formula (VII) according to any one of the alternative steps d.1) or d.2) below d.1) with one of the compounds of formula (VIII), (IX), (X) or (XI), under optional basic conditions,

 (VIII),

 (IX),

 (X),

 (XI)

wherein Z is a halogen atom or a suitable leaving group and R' is as defined in claim 1, so as to obtain the compound of formula (XII)

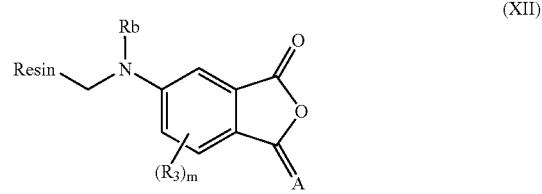
(XII)

wherein Rb is —COR', —CONHR', —COOR' or —SO₂R', respectively; or d.2) with a compound of formula (XIII)

 (XIII)

wherein Z is a halogen atom and Rb is alkyl, cycloalkyl, cycloalkylalkyl, aryl, arylalkyl, heterocyclyl or heterocyclylalkyl as defined in claim 1, so as to obtain the corresponding compound of the above formula (XII);

e) reacting the thus obtained compounds of formula (VII) or (XII) with a hydrazine compound of formula (XIV)

 (XIV)

wherein $R_2$ is as defined in claim 1, so as to obtain the compounds of formula (XV) or (XVI), respectively

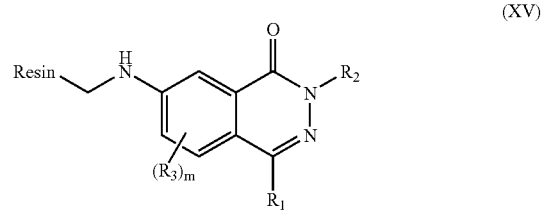
(XV)

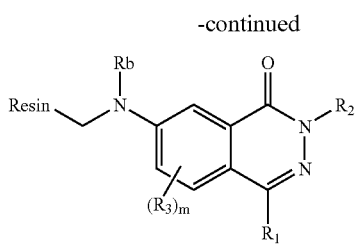

wherein Rb, $R_2$, $R_3$, m and the Resin are as above defined and $R_1$ is a group of formula —$CHR_4R_5$ or —NHR' wherein $R_4$, $R_5$ and R' are as above defined;

f) reacting the compounds of formula (XV) or (XVI) under acidic conditions so as to obtain the compound of formula (I) and, whenever desired, converting the compound of formula (I) into another compound of formula (I) and/or into a pharmaceutically acceptable salt thereof.

16. The process of claim 15 wherein, in step a), the phosphine compound is triplienylphosphine $PPh_3$.

17. The process of claim 15 wherein, in step b), the reducing agent is selected from pyridine-borane complex, sodium cyanoboron hydride, sodium triacetate boron hydride or dimethylsufide borane.

18. The process of claim 15 wherein, in step d.1), when a compound of formula (VIII), (X) or (XI) is utilized, Z is a chlorine atom.

19. The process of claim 15 wherein, in step f), acidic conditions are reached by using trifluoroacetic acid.

20. A library of two or more amino-phthalazinone compounds of formula (I)

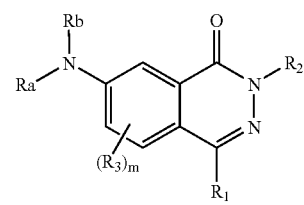

wherein
Ra and Rb are, each independently, a hydrogen atom or a group, optionally further substituted, selected from straight or branched $C_1$-$C_6$ alkyl, $C_3$-$C_6$ cycloalkyl. or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or one of Ra or Rb is hydrogen or an optionally substituted straight or branched $C_1$-$C_6$ alkyl group, and the other is a group selected from —COR', —CONHR', —COOR' or —$SO_2R'$, wherein R' is hydrogen or an optionally substituted group selected from alkyl, cycloalkyl, cycloalkylalkyl, aryl, arylalkyl, heterocyclyl or heterocyclylalkyl, as set forth above;

$R_1$ is a group of formula —$CHR_4R_5$ wherein $R_4$ and $R_5$ are, each independently, hydrogen or an optionally substituted group selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur; or $R_1$ is a group of formula —NHR', —NR'COR", —NR'CONHR" or —NR'$SO_2$R", wherein R' has the above reported meanings other than hydrogen, and R" is hydrogen or has the meanings set forth above for R';

$R_2$ is a hydrogen atom or it is a group, optionally further substituted, selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 heteroatoms selected among nitrogen, oxygen or sulfur;

any $R_3$, being placed in one or more of the free positions 5, 6 and 8 of the phthalazinone ring are, independently from each other, halogen, nitro, carboxy, cyano or a group optionally further substituted selected from straight or branched $C_1$-$C_6$ alkyl, $C_3$-$C_6$ cycloalkyl or cycloalkyl $C_1$-$C_6$ alkyl, aryl, aryl $C_1$-$C_6$ alkyl, 5 to 7 membered heterocyclyl or heterocyclyl $C_1$-$C_6$ alkyl with from 1 to 3 hetero atoms selected among nitrogen, oxygen or sulfur; or $R_3$ is a group selected from —COR', —CONHR', —$SO_2R'$, —NR'R", —NR'COR", —NR'CONHR' or —NR'$SO_2$R", wherein R' and R" are, the same or different, hydrogen or a group as set forth above;

m is 0 or an integer from 1 to 3;

or a pharmaceutically acceptable salt thereof.

21. A pharmaceutical composition comprising an amount of a compound of formula (I) as defined in claim 1 effective to treat diseases caused by and/or associated with altered protein kinase activity and, at least, one pharmaceutically acceptable excipient, carrier or diluent.

22. A pharmaceutical composition according to claim 21 further comprising one or more chemotherapeutic agents, as a combined preparation for simultaneous, separate or sequential use in anticancer therapy.

23. A product or kit comprising a compound of claim 1 or a pharmaceutical composition thereof as defined in claim 21, and one or more chemotherapeutic agents, as a combined preparation for simultaneous, separate or sequential use in anticancer therapy.

* * * * *